United States Patent
Ghose et al.

(10) Patent No.: US 11,810,648 B2
(45) Date of Patent: Nov. 7, 2023

(54) SYSTEMS AND METHODS FOR ADAPTIVE LOCAL ALIGNMENT FOR GRAPH GENOMES

(71) Applicant: Seven Bridges Genomics Inc., Charlestown, MA (US)

(72) Inventors: Kaushik Ghose, Malden, MA (US); Wan-Ping Lee, Somerville, MA (US)

(73) Assignee: Seven Bridges Genomics Inc., Charlestown, MA (US)

( * ) Notice: Subject to any disclaimer, the term of this patent is extended or adjusted under 35 U.S.C. 154(b) by 959 days.

(21) Appl. No.: 16/663,243

(22) Filed: Oct. 24, 2019

(65) Prior Publication Data
US 2020/0058374 A1  Feb. 20, 2020

Related U.S. Application Data

(63) Continuation of application No. 14/990,323, filed on Jan. 7, 2016, now abandoned.

(51) Int. Cl.
| | | |
|---|---|---|
| G01N 33/48 | (2006.01) | |
| G01N 33/50 | (2006.01) | |
| G16B 30/10 | (2019.01) | |
| G16B 30/00 | (2019.01) | |

(52) U.S. Cl.
CPC ............. G16B 30/10 (2019.02); G16B 30/00 (2019.02)

(58) Field of Classification Search
CPC ................................. G16B 30/10; G16B 30/00
See application file for complete search history.

(56) References Cited

U.S. PATENT DOCUMENTS

| | | |
|---|---|---|
| 5,511,158 A | 4/1996 | Sims |
| 5,583,024 A | 12/1996 | McElroy et al. |
| 5,674,713 A | 10/1997 | McElroy et al. |
| | (Continued) | |

FOREIGN PATENT DOCUMENTS

| | | |
|---|---|---|
| WO | WO 2007/086935 A2 | 8/2007 |
| WO | WO 2012/096579 A2 | 7/2012 |
| | (Continued) | |

OTHER PUBLICATIONS

Exam Report issued in EP14803268.3 dated Apr. 21, 2017.
(Continued)

*Primary Examiner* — Russell S Negin
(74) *Attorney, Agent, or Firm* — Wolf, Greenfield & Sacks, P.C.

(57) ABSTRACT

Systems and methods for analyzing genomic information can include obtaining a sequence read including genetic information; identifying, within a graph representing a reference genome, a plurality of candidate mapping positions that relate to the genetic information, the graph comprising nodes representing genetic sequences and edges connecting pairs of nodes; determining, by means of a computer system, whether an alignment with the graph surrounding each of the plurality of candidate mapping positions is advanced or basic; and performing for each candidate mapping position, by means of the computer system, a local alignment based on whether the local alignment is advanced or basic. The advanced local alignment can include a first-local-alignment algorithm, and the basic local alignment includes a second-local-alignment algorithm. Based on the local alignments, the mapped position of the sequence read can be identified within the genome.

19 Claims, 9 Drawing Sheets

(56) References Cited

U.S. PATENT DOCUMENTS

| | | |
|---|---|---|
| 5,700,673 A | 12/1997 | McElroy et al. |
| 5,701,256 A | 12/1997 | Marr et al. |
| 6,054,278 A | 4/2000 | Dodge et al. |
| 6,210,891 B1 | 4/2001 | Nyren et al. |
| 6,223,128 B1 | 4/2001 | Allex et al. |
| 6,306,597 B1 | 10/2001 | Macevicz |
| 6,818,395 B1 | 11/2004 | Quake et al. |
| 6,828,100 B1 | 12/2004 | Ronaghi |
| 6,833,246 B2 | 12/2004 | Balasubramanian |
| 6,890,763 B2 | 5/2005 | Jackowski et al. |
| 6,911,345 B2 | 6/2005 | Quake et al. |
| 6,925,389 B2 | 8/2005 | Hitt et al. |
| 6,989,100 B2 | 1/2006 | Norton |
| 7,169,560 B2 | 1/2007 | Lapidus et al. |
| 7,232,656 B2 | 6/2007 | Balasubramanian et al. |
| 7,282,337 B1 | 10/2007 | Harris |
| 7,577,554 B2 | 8/2009 | Lystad et al. |
| 7,580,918 B2 | 8/2009 | Chang et al. |
| 7,598,035 B2 | 10/2009 | Macevicz |
| 7,620,800 B2 | 11/2009 | Huppenthal et al. |
| 7,809,509 B2 | 10/2010 | Milosavljevic |
| 7,835,871 B2 | 11/2010 | Kain et al. |
| 7,885,840 B2 | 2/2011 | Sadiq et al. |
| 7,917,302 B2 | 3/2011 | Rognes |
| 7,960,120 B2 | 6/2011 | Rigatti et al. |
| 8,146,099 B2 | 3/2012 | Tkatch et al. |
| 8,209,130 B1 | 6/2012 | Kennedy et al. |
| 8,340,914 B2 | 12/2012 | Gatewood et al. |
| 8,370,079 B2 | 2/2013 | Sorenson et al. |
| 8,639,847 B2 | 1/2014 | Blaszczak et al. |
| 9,063,914 B2 | 6/2015 | Kural et al. |
| 9,092,402 B2 | 7/2015 | Kural et al. |
| 9,116,866 B2 | 8/2015 | Kural |
| 9,390,226 B2 | 7/2016 | Kural |
| 9,817,944 B2 | 11/2017 | Kural |
| 2002/0164629 A1 | 11/2002 | Quake et al. |
| 2004/0023209 A1 | 2/2004 | Jonasson |
| 2005/0089906 A1 | 4/2005 | Furuta et al. |
| 2006/0024681 A1 | 2/2006 | Smith et al. |
| 2006/0195269 A1 | 8/2006 | Yeatman et al. |
| 2006/0292611 A1 | 12/2006 | Berka et al. |
| 2007/0114362 A1 | 5/2007 | Feng et al. |
| 2007/0166707 A1 | 7/2007 | Schadt et al. |
| 2008/0077607 A1 | 3/2008 | Gatawood et al. |
| 2008/0251711 A1 | 10/2008 | Reilly |
| 2008/0294403 A1 | 11/2008 | Zhu et al. |
| 2009/0026082 A1 | 1/2009 | Rothberg et al. |
| 2009/0119313 A1 | 5/2009 | Pearce |
| 2009/0127589 A1 | 5/2009 | Rothberg et al. |
| 2009/0164135 A1 | 6/2009 | Brodzik et al. |
| 2009/0191565 A1 | 7/2009 | Lapidus et al. |
| 2009/0300781 A1 | 12/2009 | Bancroft et al. |
| 2010/0010992 A1 | 1/2010 | Morris |
| 2010/0035252 A1 | 2/2010 | Rothberg et al. |
| 2010/0041048 A1 | 2/2010 | Diehi et al. |
| 2010/0137143 A1 | 6/2010 | Rothberg et al. |
| 2010/0169026 A1 | 7/2010 | Sorenson et al. |
| 2010/0188073 A1 | 7/2010 | Rothberg et al. |
| 2010/0197507 A1 | 8/2010 | Rothberg et al. |
| 2010/0240046 A1 | 9/2010 | Palmer et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0004413 A1 | 1/2011 | Carnevali et al. |
| 2011/0009278 A1 | 1/2011 | Kain et al. |
| 2011/0098193 A1 | 4/2011 | Kingsmore et al. |
| 2011/0207135 A1 | 8/2011 | Faham et al. |
| 2012/0030566 A1 | 2/2012 | Victor |
| 2012/0040851 A1 | 2/2012 | Lieberman et al. |
| 2012/0041727 A1 | 2/2012 | Mishra et al. |
| 2012/0045771 A1 | 2/2012 | Beier et al. |
| 2012/0239706 A1 | 9/2012 | Steinfadt |
| 2012/0330566 A1 | 12/2012 | Chaisson |
| 2013/0029879 A1 | 1/2013 | Shelly et al. |
| 2013/0035904 A1 | 2/2013 | Kuhn |
| 2013/0059738 A1 | 3/2013 | Leamon et al. |
| 2013/0059740 A1 | 3/2013 | Drmanac et al. |
| 2013/0073214 A1 | 3/2013 | Hyland et al. |
| 2013/0124100 A1 | 5/2013 | Drmanac et al. |
| 2013/0289099 A1 | 10/2013 | Goff et al. |
| 2013/0311106 A1 | 11/2013 | White et al. |
| 2014/0012866 A1 | 1/2014 | Bowman et al. |
| 2014/0025312 A1 | 1/2014 | Chin et al. |
| 2014/0051588 A9 | 2/2014 | Drmanac et al. |
| 2014/0066317 A1 | 3/2014 | Talasaz |
| 2014/0129201 A1 | 5/2014 | Kennedy et al. |
| 2014/0136120 A1 | 5/2014 | Colwell et al. |
| 2014/0200147 A1 | 7/2014 | Bartha et al. |
| 2014/0278590 A1 | 9/2014 | Abbassi et al. |
| 2014/0280360 A1 | 9/2014 | Webber et al. |
| 2014/0323320 A1 | 10/2014 | Jia et al. |
| 2015/0056613 A1 | 2/2015 | Kural |
| 2015/0057946 A1 | 2/2015 | Kural |
| 2015/0094212 A1 | 4/2015 | Gottimukkala et al. |
| 2015/0110754 A1 | 4/2015 | Bai et al. |
| 2015/0112602 A1 | 4/2015 | Kural et al. |
| 2015/0112658 A1 | 4/2015 | Kural et al. |
| 2015/0197815 A1 | 7/2015 | Kural |
| 2015/0199472 A1 | 7/2015 | Kural |
| 2015/0199473 A1 | 7/2015 | Kural |
| 2015/0199474 A1 | 7/2015 | Kural |
| 2015/0199475 A1 | 7/2015 | Kural |
| 2015/0227685 A1 | 8/2015 | Kural |
| 2015/0293994 A1 | 10/2015 | Kelly |
| 2015/0302145 A1 | 10/2015 | Kural et al. |
| 2015/0310167 A1 | 10/2015 | Kural et al. |
| 2015/0344970 A1 | 12/2015 | Vogelstein et al. |
| 2015/0347678 A1 | 12/2015 | Kural |
| 2015/0356147 A1 | 12/2015 | Mishra et al. |
| 2016/0259880 A1 | 9/2016 | Semenyuk |
| 2016/0306921 A1 | 10/2016 | Kural |
| 2016/0364523 A1 | 12/2016 | Locke et al. |
| 2017/0058320 A1 | 3/2017 | Locke et al. |
| 2017/0058341 A1 | 3/2017 | Locke et al. |
| 2017/0058365 A1 | 3/2017 | Locke et al. |
| 2017/0198351 A1 | 7/2017 | Lee et al. |
| 2017/0199959 A1 | 7/2017 | Locke |
| 2017/0199960 A1 | 7/2017 | Ghose et al. |
| 2017/0242958 A1 | 8/2017 | Brown |

FOREIGN PATENT DOCUMENTS

| | | |
|---|---|---|
| WO | WO 2012/098515 A1 | 7/2012 |
| WO | WO 2012/142531 A2 | 10/2012 |
| WO | WO 2015/027050 A1 | 2/2015 |
| WO | WO 2015/048753 A1 | 4/2015 |
| WO | WO 2015/058093 A1 | 4/2015 |
| WO | WO 2015/058095 A1 | 4/2015 |
| WO | WO 2015/058097 A1 | 4/2015 |
| WO | WO 2015/058120 A1 | 4/2015 |
| WO | WO 2015/061099 A1 | 4/2015 |
| WO | WO 2015/061103 A1 | 4/2015 |
| WO | WO 2015/105963 A1 | 7/2015 |
| WO | WO 2015/123269 A1 | 8/2015 |
| WO | WO 2016/141294 A1 | 9/2016 |
| WO | WO 2016/201215 A1 | 12/2016 |
| WO | WO 2017/120128 A1 | 7/2017 |
| WO | WO 2017/123864 A1 | 7/2017 |
| WO | WO 2017/147124 A1 | 8/2017 |

OTHER PUBLICATIONS

Examination Report issued in SG 11201601124Y dated Mar. 1, 2018.

Extended European Search Report issued in EP 14837955.5 dated Mar. 29, 2017.

Extended European Search Report issued in EP 14847490.1 dated May 9, 2017.

Extended European Search Report issued in EP 14854801.9 dated Apr. 12, 2017.

(56) References Cited

OTHER PUBLICATIONS

International Search Report and Written Opinion for International Patent Application No. PCT/US2014/061158 dated Feb. 4, 2015.
International Search Report and Written Opinion for International Application No. PCT/US2014/058328, dated Dec. 30, 2014.
International Search Report and Written Opinion for International Patent Application No. PCT/US2014/061198, dated Feb. 4, 2015.
International Search Report and Written Opinion for International Application No. PCT/US2014/061162 dated Mar. 19, 2015.
International Search Report and Written Opinion for application No. PCT/US2016/057324 dated Jan. 10, 2017.
International Search Report and Written Opinion for International Application No. PCT/US2016/036873 dated Sep. 7, 2016.
International Search Report and Written Opinion for International Patent Application No. PCT/US2014/061156 dated Feb. 17, 2015.
International Preliminary Report on Patentability issued in application No. PCT/US2014/052065 dated Feb. 23, 2016.
International Search Report and Written Opinion for International Patent Application No. PCT/US2014/052065 dated Dec. 11, 2014.
International Search Report and Written Opinion for International Application No. PCT/US2014/060680 dated Jan. 27, 2015.
International Search Report and Written Opinion for International Patent Application No. PCT/US2014/060690 dated Feb. 10, 2015.
International Search Report and Written Opinion for International Application No. PCT/US2015/010604 dated Mar. 31, 2015.
International Search Report and Written Opinion for International Patent Application No. PCT/US2015/015375 dated May 11, 2015.
International Search Report and Written Opinion for International Patent Application No. PCT/US2016/020899 dated May 5, 2016.
International Search Report and Written Opinion for International Patent Application No. PCT/US2017/013329 dated Apr. 7, 2017.
International Search Report and Written Opinion for International Application No. PCT/US2017/012015 dated Apr. 19, 2017.
International Search Report and Written Opinion for International Application No. PCT/US2017/018830 dated Aug. 31, 2017.
International Search Report and Written Opinion dated Sep. 2, 2016, for International Patent Application No. PCT/US2016/033201 with International Filing Date May 19, 2016 (14 pages).
Written Opinion issued in SG 11201601124Y dated Dec. 21, 2016.
Written Opinion issued in SG 11201602903X dated May 29, 2017.
Written Opinion issued in SG 11201603039P dated Jun. 12, 2017.
Written Opinion issued in SG 11201603044S dated Sep. 10, 2017.
Written Opinion issued in SG 11201605506Q dated Jun. 15, 2017.
Agarwal et al., Social interaction network extractor from text. InThe Companion Volume of the Proceedings of IJCNLP 2013: System Demonstrations Oct. 2013: pp. 33-36.
Aguiar et al., HapCompass: a fast cycle basis algorithm for accurate haplotype assembly of sequence data. Journal of Computational Biology. Jun. 1, 2012;19(6):577-90.
Aguiar et al., Haplotype assembly in polyploid genomes and identical by descent shared tracts. Bioinformatics. Jun. 19, 2013;29(13):i352-60.
Airoldi et al., Mixed membership stochastic blockmodels. Journal of machine learning research. Sep. 9, 2008:1981-2014.
Albers et al., accurate indel calls from short-read data. Genome research. Jun. 1, 2011;21(6):961-73.
Alioto et al., A comprehensive assessment of somatic mutation detection in cancer using whole-genome sequencing. Nature communications. Dec. 9, 2015;6:10001.
Altera, Implementation of the Smith-Waterman algorithm on reconfigurable supercomputing platform, White Paper ver 1.0. 2007 (18 pages).
Altschul et al., Optimal sequence alignment using affine gap costs. Bulletin of mathematical biology. Jan. 1, 1986;48(5-6):603-16.
Bansal et al., An MCMC algorithm for haplotype assembly from whole-genome sequence data. Genome research. Aug. 1, 2008; 18(8):1336-46.
Bao et al., Branch: boosting RNA-Seq assemblies with partial or related genomic sequences. Bioinformatics. Mar. 14, 2013;29(10):1250-9.

Barbieri et al., Exome sequencing identifies recurrent SPOP, FOXA1 and MED12 mutations in prostate cancer. Nature genetics. Jun. 2012;44(6):685-689.
Beerenwinkel N, Eriksson N, Sturmfels B. Conjunctive bayesian networks. Bernoulli. 2007;13(4):893-909.
Berlin et al., Assembling large genomes with single-molecule sequencing and locality-sensitive hashing. Nature biotechnology. Jun. 2015;33(6):623.bioRxiv preprint (35 pages); retrieved from the internet on Jan. 29, 2015, at <http://biorxiv.org/content/biorxiv/early/2014/08/14/008003.full.pdf>.
Bertone et al., Global identification of human transcribed sequences with genome tiling arrays. Science. Dec. 24, 2004;306(5705):2242-6.
Bertrand et al., Genetic map refinement using a comparative genomic approach. Journal of Computational Biology. Oct. 1, 2009;16(10):1475-86.
Black, A simple answer for a splicing conundrum. Proceedings of the National Academy of Sciences. Apr. 5, 2005;102(14):4927-8.
Boyer et al., A fast string searching algorithm. Communications of the ACM. Oct. 1, 1977;20(10):762-72.
Browning et al., Haplotype phasing: existing methods and new developments. Nature Reviews Genetics. Oct. 2011;12(10):703.
Buhler et al., Search algorithms for biosequences using random projection. University of Washington; Aug. 2001. (203 pages); retreived from the internet on Jun. 3, 2016, at <http://www.mathcs.emory.edu/~cheung/papers/Matching/Search-Alg-for-Biosequences-Thesis.pdf>.
Caboche et al., Comparison of mapping algorithms used in high-throughput sequencing: application to Ion Torrent data. BMC genomics. Dec. 2014;15(1):264.
Carig et al., Ordering of cosmid clones covering the herpes simplex virus type I (HSV-I) genome: a test case for fingerprinting by hybridisation. Nucleic acids research. May 1, 1990;18(9):2653-60.
Carrington et al., Polypeptide ligation occurs during post-translational modification of concanavalin A. Nature. Jan. 1985;313(5997):64.
Cartwright, DNA assembly with gaps (Dawg): simulating sequence evolution. Bioinformatics. Nov. 1, 2005;21(Suppl_3):iii31-8.
Chang et al., The application of alternative splicing graphs in quantitative analysis of alternative splicing form from EST database, Int J Comp Appl Tech. 2005; 22(1):14.
Chin et al., Nonhybrid, finished microbial genome assemblies from long-read SMRT sequencing data. Nature methods. Jun. 2013;10(6):563-571.
Chuang et al., Gene recognition based on DAG shortest paths. Bioinformatics. Jun. 1, 2001;17(suppl_1):S56-64.
Compeaut et al., How to apply de Bruijn graphs to genome assembly. Nature biotechnology. Nov. 2011;29(11):987-991.
Costa, Uncovering the Complexity of Transcriptomes with RNA-Seq, J Biomed Biotech. 2010; 853916:1-19.
Craddock et al., Wellcome Trust Case Control Consortium. Genome-wide association study of 14,000 cases of seven common diseases and 3,000 shared controls. Nature. May 11, 2007;447:661-78.
Danecek et al., The variant call format and VCFtools. Bioinformatics. Jun. 7, 2011;27(15):2156-8.
Delcher et al., Alignment of whole genomes. Nucleic acids research. Jan. 1, 1999;27(11):2369-76.
Denoeud et al., Identification of polymorphic tandem repeats by direct comparison of genome sequence from different bacterial strains: a web-based resource. BMC bioinformatics. Dec. 2004;5(1):4.
Depristo et al., A framework for variation discovery and genotyping using next-generation DNA sequencing data. Nature genetics. May 2011;43(5):491-498.
Duan et al., Optimizing de novo common wheat transcriptome assembly using short-read RNA-Seq data. BMC genomics. Dec. 2012;13(1):392.
Dudley et al., A quick guide for developing effective bioinformatics programming skills. PLOS computational biology. Dec. 24, 2009;5(12):e1000589.
Durbin, Efficient haplotype matching and storage using the positional Burrows-Wheeler transform (PBWT). Bioinformatics. Jan. 9, 2014;30(9):1266-72.

(56) References Cited

OTHER PUBLICATIONS

Durham et al., EGene: a configurable pipeline generation system for automated sequence analysis. Bioinformatics. Apr. 6, 2005;21(12):2812-3.
Endelman JB. New algorithm improves fine structure of the barley consensus SNP map. BMC genomics. Dec. 2011;12(1):407.
Farrar, Striped Smith-Waterman speeds database searches six times over other SIMD implementations. Bioinformatics. Nov. 16, 2006;23(2):156-61.
Fitch, Distinguishing homologous from analogous proteins. Systematic zoology. Jun. 1, 1970;19(2):99-113.
Flicek et al., Sense from sequence reads: methods for alignment and assembly. Nature methods. Oct. 15, 2009;6(11s):S6-S12.
Florea et al., Gene and alternative splicing annotation with AIR. Genome research. Jan. 1, 2005;15(1):54-66.
Florea et al., Genome-guided transcriptome assembly in the age of next-generation sequencing. IEEE/ACM Transactions on Computational Biology and Bioinformatics (TCBB). Sep. 1, 2013;10(5):1234-40.
Garber et al., Computational methods for transcriptome annotation and quantification using RNA-seq. Nature methods. Jun. 2011;8(6):469-477.
Gerhnger et al., Intratumor heterogeneity and branched evolution revealed by multiregion sequencing. New England journal of medicine. Mar. 8, 2012;366(10):883-92.
Golub et al., Molecular classification of cancer: class discovery and class prediction by gene expression monitoring, science. Oct. 15, 1999;286(5439):531-7.
Goto et al., BioRuby: bioinformatics software for the Ruby programming language. Bioinformatics. Aug. 25, 2010;26(20):2617-9.
Gotoh, Multiple sequence alignment: algorithms and applications. Advances in biophysics. Jan. 1, 1999;36:159-206.
Gotoh., An improved algorithm for matching biological sequences. Journal of molecular biology. Dec. 15, 1982;162(3):705-8.
Grabherr et al., Full-length transcriptome assembly from RNA-Seq data without a reference genome. Nature biotechnology. Jul. 2011;29(7):644-654.
Grasso et al., Combining partial order alignment and progressive multiple sequence alignment increases alignment speed and scalability to very large alignment problems. Bioinformatics. Feb. 12, 2004;20(10):1546-56.
Guttman et al., Ab initio reconstruction of cell type-specific transcriptomes in mouse reveals the conserved multi-exonic structure of lincRNAs. Nature biotechnology. May 2010;28(5):503-510.
Guttman, Ab initio reconstruction of transcriptomes of pluripotent and lineage committed cells reveals gene structures of thousands of lincRNAs, NIH-PA Author Manuscript. 2010.
Haas et al., DAGchainer: a tool for mining segmental genome duplications and synteny. Bioinformatics. Jul. 9, 2004;20(18):3643-6.
HapMap International Consortium. A haplotype map of the human genome. Nature. 2005;437:1299-320.
Harrow et al., Gencode: the reference human genome annotation for The Encode Project. Genome research. Sep. 1, 2012;22(9):1760-74.
He et al., Optimal algorithms for haplotype assembly from whole-genome sequence data. Bioinformatics. Jun. 1, 2010;26(12):i183-90.
Heber et al., Splicing graphs and EST assembly problem. Bioinformatics. Jul. 1, 2002;18(suppl_1):S181-8.
Hein, A new method that simultaneously aligns and reconstructs ancestral sequences for any number of homologous sequences, when the phylogeny is given. Molecular Biology and Evolution. Nov. 1, 1989;6(6):649-68.
Hein, A tree reconstruction method that is economical in the number of pairwise comparisons used. Molecular biology and evolution. Nov. 1, 1989;6(6):649-84.
Holland et al., Bio Java: an open-source framework for bioinformatics. Bioinformatics. Aug. 8, 2008;24(18):2096-7.
Homer et al., Improved variant discovery through local re-alignment of short-read next-generation sequencing data using SRMA. Genome biology. Oct. 2010;11(10):R99.
Hoon et al., Biopipe: a flexible framework for protocol-based bioinformatics analysis. Genome Research. Aug. 1, 2003;13(8):1904-15.
Horspool, Practical fast searching in strings. Software: Practice and Experience. Jun. 1980;10(6):501-6.
Huang, Chapter 3: Bio-Sequence Comparison and Alignment, ser. Curr Top Comp Mol Biol. Cambridge, Mass.: The MIT Press. 2002:45-69.
Hutchinson et al., Allele-specific methylation occurs at genetic variants associated with complex disease. PloS one. Jun. 9, 2014;9(6):e98464.
Kano et al., Text mining meets workflow: linking U-Compare with Taverna. Bioinformatics. Aug. 12, 2010;26(19):2486-7.
Kehr et al., Genome alignment with graph data structures: a comparison. BMC bioinformatics. Dec. 2014;15(1):99.
Kent, BLAT—the BLAST-like alignment tool. Genome research. Apr. 1, 2002;12(4):656-64.
Kim et al., ECgene: genome-based EST clustering and gene modeling for alternative splicing. Genome research. Apr. 1, 2005;15(4):566-76.
Kim et al., TopHat2: accurate alignment of transcriptomes in the presence of insertions, deletions and gene fusions. Genome biology. Apr. 2013;14(4):R36.
Kim PG, Cho HG, Park K. A scaffold analysis tool using mate-pair information in genome sequencing. BioMed Research International. Apr. 3, 2008; 8(3): 195-197.
Koolen et al., Clinical and molecular delineation of the 17q21.31 microdeletion syndrome. Journal of medical genetics. Nov. 1, 2008;45(11):710-20.
Kumar et al., Comparing de novo assemblers for 454 transcriptome data. BMC genomics. Dec. 2010;11(1):571.
Kurtz et al., Versatile and open software for comparing large genomes. Genome biology. Jan. 2004;5(2):R12.
Laframboise, Single nucleotide polymorphism arrays: a decade of biological, computational and technological advances. Nucleic acids research. Jul. 1, 2009;37(13):4181-93.
Lam et al., Compressed indexing and local alignment of DNA. Bioinformatics. Jan. 28, 2008;24(6):791-7.
Langmead et al., Ultrafast and memory-efficient alignment of short DNA sequences to the human genome. Genome biology. Mar. 2009;10(3):R25.
Larkin et al., Clustal W and Clustal X version 2.0. bioinformatics. Nov. 1, 2007;23(21):2947-8.
Lecca et al., Defining order and timing of mutations during cancer progression: the TO-DAG probabilistic graphical model. Frontiers in genetics. Oct. 13, 2015;6:309: 1-17.
Lee et al. Accurate read mapping using a graph-based human pan-genome. (May 2015) American Society of Human Genetics 64th Annual Meeting Platform Abstracts; Abstract 41.
Lee et al., MOSAIK: a hash-based algorithm for accurate next-generation sequencing short-read mapping. PLoS one. Mar. 5, 2014;9(3):e90581.
Lee et al., Multiple sequence alignment using partial order graphs. Bioinformatics. Mar. 1, 2002;18(3):452-64.
Lee, 2014, Accurate read mapping using a graph-based human pan-genome, ASHG 2014 Abstracts.
Lee, Bioinformatics analysis of alternative splicing, Brief Bioinf. 2005;6(1):23-33.
Lee, Generating consensus sequences from partial order multiple sequence alignment graphs. Bioinformatics. May 22, 2003;19(8):999-1008.
Legault et al., Inference of alternative splicing from RNA-Seq data with probabilistic splice graphs. Bioinformatics. Jul. 11, 2013;29(18):2300-10.
Legault, 2010, Learning Probalistic Splice Graphs from RNA-Seq data, pages.cs.wisc.edu/~legault/cs760_writeup.pdf; retrieved from the internet on Apr. 6, 2014.
Leipzig et al., The Alternative Splicing Gallery (ASG): bridging the gap between genome and transcriptome. Nucleic Acids Research. Jan. 1, 2004;32(13):3977-83.

(56) References Cited

OTHER PUBLICATIONS

Li et al., A survey of sequence alignment algorithms for next-generation sequencing. Briefings in bioinformatics. Sep. 1, 2010;11(5):473-83.
Li et al., Fast and accurate short read alignment with Burrows-Wheeler transform. bioinformatics. Jul. 15, 2009;25(14):1754-60.
Li et al., SOAP: short oligonucleotide alignment program. Bioinformatics. Jan. 28, 2008;24(5):713-4.
Li et al., SOAP2: an improved ultrafast tool for short read alignment. Bioinformatics. Jun. 3, 2009;25(15):1966-7.
Li et al., The sequence alignment/map format and SAMtools. Bioinformatics. Aug. 15, 2009;25(16):2078-9.
Lindgreen, AdapterRemoval: easy cleaning of next-generation sequencing reads. BMC research notes. Dec. 2012;5(1):337.
Lipman et al., Rapid and sensitive protein similarity searches. Science. Mar. 22, 1985;227(4693):1435-41.
Lücking et al., PICS-Ord: unlimited coding of ambiguous regions by pairwise identity and cost scores ordination. BMC bioinformatics. Dec. 2011;12(1):10.
Lupski et al., Genomic disorders: molecular mechanisms for rearrangements and conveyed phenotypes. PLoS genetics. Dec. 30, 2005;1(6):e49.
Ma et al., Multiple genome alignment based on longest path in directed acyclic graphs. International journal of bioinformatics research and applications. Oct. 1, 2010;6(4):366-83.
Mamoulis, 2004, Non-contiguous sequence pattern queries, in Advances in Database Technology—EDBT 2004: 9th International Conference on Extending Database Technology, Heraklion, Crete, Greece, Mar. 14-18, 2004, Proceedings (18 pages); retreived from the internet on Jun. 3, 2016, at <http://I.cs.hku.hk/~nikos/seqjoin.pdf>.
Manolio, Genomewide association studies and assessment of the risk of disease. New England journal of medicine. Jul. 8, 2010;363(2):166-76.
Mardis, The $1,000 genome, the $100,000 analysis?, Genome Med. 2010;2(11):84-85.
Margulies et al., Genome sequencing in microfabricated high-density picolitre reactors. Nature. Sep. 2005;437(7057):376-380.
Marth et al., A general approach to single-nucleotide polymorphism discovery. Nature genetics. Dec. 1999;23(4):452-456.
Mazrouee et al., FastHap: fast and accurate single individual haplotype reconstruction using fuzzy conflict graphs. Bioinformatics. Aug. 22, 2014;30(17):i371-8.
McSherry, Spectral partitioning of random graphs. Proceedings 42nd IEEE Symposium on Foundations of Computer Science. Oct. 8, 2001:529-537.
Miller et al., Assembly algorithms for next-generation sequencing data. Genomics. Jun. 1, 2010;95(6):315-27.
Misra et al., Anatomy of a hash-based long read sequence mapping algorithm for next generation DNA sequencing. Bioinformatics. Nov. 18, 2010;27(2):189-95.
Mount, Multiple Sequence Alignment, Bioinformatics, 2001, Cold Spring Harbor Laboratory Press, Cold Spring Harbor, New York. 2001:139-204.
Mourad et al., A hierarchical Bayesian network approach for linkage disequilibrium modeling and data-dimensionality reduction prior to genome-wide association studies. BMC bioinformatics. Dec. 2011;12(1):16:1-20.
Myers, The fragment assembly string graph. Bioinformatics. Jan. 1, 2005;21(suppl_2):ii79-85.
Nagalakshnu et al., RNA-Seq: a method for comprehensive transcriptome analysis. Current protocols in molecular biology. Jan. 2010;89(1):4-11.
Nagarajann, Pop M. Sequence assembly demystified. Nature Reviews Genetics. Mar. 2013;14(3):157-167.
Nakao et al., Large-scale analysis of human alternative protein isoforms: pattern classification and correlation with subcellular localization signals. Nucleic acids research. Jan. 1, 2005;33(8):2355-63.

Needleman et al., A general method applicable to the search for similarities in the amino acid sequence of two proteins. Journal of molecular biology. Mar. 28, 1970;48(3):443-53.
Newman et al., An ultrasensitive method for quantitating circulating tumor DNA with broad patient coverage. Nature medicine. May 2014;20(5):548: 1-11.
Newman ME. Community detection and graph partitioning. arXiv:1305.4974v1. EPL (Emophysics Letters). Aug. 9, 2013;103(2):28003.
Ning et al., SSAHA: a fast search method for large DNA databases. Genome research. Oct. 1, 2001;11(10):1725-9.
Olsson et al., Serial monitoring of circulating tumor DNA in patients with primary breast cancer for detection of occult metastatic disease. EMBO molecular medicine. Aug. 1, 2015;7(8):1034-47.
Oshiack et al., From RNA-seq reads to differential expression results. Genome biology. Dec. 2010;11(12):220.
Parks et al., Detecting non-allelic homologous recombination from high-throughput sequencing data. Genome biology. Dec. 2015;16(1):72.
Pearson et al., Improved tools for biological sequence comparison. Proceedings of the National Academy of Sciences. Apr. 1, 1988;85(8):2444-8.
Pe'er et al., Evaluating and improving power in whole-genome association studies using fixed marker sets. Nature genetics. Jun. 2006;38(6):663-667.
Peixoto, Efficient Monte Carlo and greedy heuristic for the inference of stochastic block models. Physical Review E. Jan. 13, 2014;89(1):012804.
Pop et al., Comparative genome assembly. Briefings inbioinformatics. Sep. 1, 2004;5(3):237-48.
Potter et al., ASC: An associative-computing paradigm. Computer. Nov. 1994;27(11):19-25.
Pruesse et al., SINA: accurate high-throughput multiple sequence alignment of ribosomal RNA genes. Bioinformatics. May 3, 2012;28(14):1823-9.
Quail et al., A tale of three next generation sequencing platforms: comparison of Ion Torrent, Pacific Biosciences and Illumina MiSeq sequencers. BMC genomics. Dec. 2012;13(1):341.
Rajaram et al., Pearl millet [*Pennisetum glaucum* (L.) R. Br.] consensus linkage map constructed using four RIL mapping populations and newly developed EST-SSRs. BMC genomics. Dec. 2013;14(1):159.
Raphael et al., A novel method for multiple alignment of sequences with repeated and shuffled elements. Genome Research. Nov. 1, 2004;14(11):2336-46.
Robertson et al., De novo assembly and analysis of RNA-seq data. Nature methods. Nov. 2010;7(11):909.
Rodelsperger et al., Syntenator: multiple gene order alignments with a gene-specific scoring function. Algorithms for Molecular Biology. Dec. 2008;3(1):14.
Rognes et al., Six-fold speed-up of Smith-Waterman sequence database searches using parallel processing on common microprocessors. Bioinformatics. Aug. 1, 2000;16(8):699-706.
Rognes, Faster Smith-Waterman database searches with inter-sequence SIMD parallelisation. BMC bioinformatics. Dec. 2011;12(1):221.
Rognes, ParAlign: a parallel sequence alignment algorithm for rapid and sensitive database searches. Nucleic acids research. Apr. 1, 2001;29(7):1647-52.
Ronquist et al., MrBayes 3.2: efficient Bayesian phylogenetic inference and model choice across a large model space. Systematic biology. May 1, 2012;61(3):539-42.
Rothberg et al., An integrated semiconductor device enabling non-optical genome sequencing. Nature. Jul. 2011;475(7356):348-352.
Saebøet et al., Paralign: rapid and sensitive sequence similarity searches powered by parallel computing technology. Nucleic acids research. Jul. 1, 2005;33(suppl_2):W535-9.
Sato et al., Directed acyclic graph kernels for structural RNA analysis. BMC bioinformatics. Dec. 2008;9(1):318.
Schneeberger et al., Simultaneous alignment of short reads against multiple genomes. Genome biology. Sep. 2009;10(9):R98.2-R98.12.
Schwikowski et al., Weighted sequence graphs: boosting iterated dynamic programming using locally suboptimal solutions. Discrete Applied Mathematics. Apr. 1, 2003;127(1):95-117.

(56) References Cited

OTHER PUBLICATIONS

Shao et al., Bioinformatic analysis of exon repetition, exon scrambling and trans-splicing in humans. Bioinformatics. Nov. 24, 2005;22(6):692-8.
Sievers et al., Fast, scalable generation of high-quality protein multiple sequence alignments using Clustal Omega. Molecular systems biology. Jan. 1, 2011;7(1):539.
Slater et al., Automated generation of heuristics for biological sequence comparison. BMC bioinformatics. Dec. 2005;6(1):31.
Smith et al., Identification of common molecular subsequences. Journal of molecular biology. Mar. 25, 1981;147(1):195-7.
Smith et al., Multiple insert size paired-end sequencing for deconvolution of complex transcriptomes. RNA biology. May 1, 2012;9(5):596-609.
Soni et al., Progress toward ultrafast DNA sequencing using solid-state nanopores. Clinical chemistry. Nov. 1, 2007;53(11):1996-2001.
Sosa et al., Next-generation sequencing of human mitochondrial reference genomes uncovers high heteroplasmy frequency. PLoS computational biology. Oct. 25, 2012;8(10):e1002737.
Stephens et al., A new statistical method for haplotype reconstruction from population data. The American Journal of Human Genetics. Apr. 1, 2001;68(4):978-89.
Stewart et al., A comprehensive map of mobile element insertion polymorphisms in humans. PLoS genetics. Aug. 18, 2011;7(8):e1002236.
Sturgeon et al., Rcda: A highly sensitive and specific alternatively spliced transcript assembly tool featuring upstream consecutive exon structures. Genomics. Dec. 1, 2012;100(6):357-62.
Subramanian et al., DIALIGN-TX: greedy and progressive approaches for segment-based multiple sequence alignment. Algorithms for Molecular Biology. Dec. 2008;3(1):1-11.
Sudmant et al., An integrated map of structural variation in 2,504 human genomes. Nature. Oct. 2015;526(7571):75-81.
Sun, Pairwise comparison between genomic sequences and optical-maps (Doctoral dissertation, New York University, Graduate School of Arts and Science, 131 pages); retreived from the internet on Jun. 3, 2016, at <https://cs.nyu.edu/mishra/PEOPLE/sun_bing.pdf>.
Szalkowski et al., Graph-based modeling of tandem repeats improves global multiple sequence alignment. Nucleic acids research. Jul. 22, 2013;41(17):e162.
Szalkowski, Fast and robust multiple sequence alignment with phylogeny-aware gap placement. BMC bioinformatics. Dec. 2012;13(1):129.
Tarhio et al., Approximate boyer-moore string matching. SIAM Journal on Computing. Apr. 1993;22(2):243-60.
Thomas, Community-wide effort aims to better represent variation in human reference genome, Genome Web 2014;11 pages.
Trapnell et al., TopHat: discovering splice junctions with RNA-Seq. Bioinformatics. May 1, 2009;25(9):1105-11.
Trapnell et al., Transcript assembly and abundance estimation from RNA-Seq reveals thousands of new transcripts and switching among isoforms. Nature biotechnology. May 2010;28(5):511-515.
Uchiyama et al., CGAT: a comparative genome analysis tool for visualizing alignments in the analysis of complex evolutionary changes between closely related genomes. BMC bioinformatics. Dec. 2006;7(1):472.
Wang et al., Next generation sequencing has lower sequence coverage and poorer SNP-detection capability in the regulatory regions. Scientific reports. Aug. 5, 2011;1:55.
Wang et al., RNA-Seq: a revolutionary tool for transcriptomics. Nature reviews genetics. Jan. 2009;10(1):57-63.
Waterman et al., Some biological sequence metrics. Advances in Mathematics. Jun. 1, 1976;20(3):367-87.
Wu et al., Fast and SNP-tolerant detection of complex variants and splicing in short reads. Bioinformatics. Feb. 10, 2010;26(7):873-81.
Xing et al., An expectation-maximization algorithm for probabilistic reconstructions of full-length isoforms from splice graphs. Nucleic acids research. Jan. 1, 2006;34(10):3150-60.
Yang et al., Leveraging reads that span multiple single nucleotide polymorphisms for haplotype inference from sequencing data. Bioinformatics. Jul. 3, 2013;29(18):2245-52.
Yanovsky et al., Read mapping algorithms for single molecule sequencing data. In International Workshop on Algorithms in Bioinformatics Sep. 15, 2008 (pp. 38-49). Springer, Berlin, Heidelberg.
Yu et al., A tool for creating and parallelizing bioinformatics pipelines. In2007 DoD High Performance Computing Modernization Program Users Group Conference Jun. 18, 2007 (pp. 417-420). IEEE.
Yu et al., The construction of a tetrapioid cotton genome wide comprehensive reference map. Genomics. Apr. 1, 2010;95(4):230-40.
Zeng et al., PyroHMMvar: a sensitive and accurate method to call short indels and SNPs for Ion Torrent and 454 data. Bioinformatics. Aug. 31, 2013;29(22):2859-68.
Zhang et al., Construction of a high-density genetic map for sesame based on large scale marker development by specific length amplified fragment (SLAF) sequencing. BMC plant biology. Dec. 2013;13(1):141.
U.S. Appl. No. 14/990,323, filed Jan. 7, 2016, Ghose et al.
PCT/US2016/033201, Sep. 2, 2016, International Search Report and Written Opinion.
PCT/US2014/061158, Feb. 4, 2015, International Search Report and Written Opinion.
EP14847490.1, May 9, 2017, Extended European Search Report and Written Opinion.
PCT/US2014/058328, Dec. 30, 2014, International Search Report and Written Opinion.
PCT/US2014/061198, Feb. 4, 2015, International Search Report and Written Opinion.
EP14803268.3, Apr. 21, 2017, Exam Report.
SG11201603039P, Jun. 12, 2017, Written Opinion.
PCT/US2014/061162, Mar. 19, 2015, International Search Report and Written Opinion.
PCT/US2016/057324, Jan. 10, 2017, International Search Report and Written Opinion.
PCT/US2016/036873, Sep. 7, 2016, International Search Report and Written Opinion.
EP14854801.9, Apr. 12, 2017, Extended European Search Report and Written Opinion.
SG11201602903X, May 29, 2017, Written Opinion.
PCT/US2014/061156, Feb. 17, 2015, International Search Report and Written Opinion.
EP14837955.5, Mar. 29, 2017, Extended European Search Report and Written Opinion.
SG11201601124Y, Mar. 1, 2018, Examination Report.
SG11201601124Y, Dec. 21, 2016, Written Opinion.
PCT/US2014/052065, Dec. 11, 2014, International Search Report and Written Opinion.
PCT/US2014/052065, Feb. 23, 2016, International Search Report and Written Opinion.
PCT/US2014/060680, Jan. 27, 2015, International Search Report and Written Opinion.
SG11201603044S, Sep. 10, 2017, Written Opinion.
PCT/US2014/060690, Feb. 10, 2015, International Search Report and Written Opinion.
SG11201605506Q, Jun. 15, 2017, Written Opinion.
PCT/US2015/010604, Mar. 31, 2015, International Search Report and Written Opinion.
PCT/US2015/015375, May 11, 2015, International Search Report and Written Opinion.
PCT/US2016/020899, May 5, 2016, International Search Report and Written Opinion.
PCT/US2017/013329, Apr. 7, 2017, International Search Report and Written Opinion.
PCT/US2017/012015, Apr, 19, 2017, International Search Report and Written Opinion.
PCT/US2017/018830, Aug. 31, 2017, International Search Report and Written Opinion.

SYSTEMS AND METHODS FOR ADAPTIVE LOCAL ALIGNMENT FOR GRAPH GENOMES

RELATED APPLICATIONS

This Application is a Continuation of U.S. application Ser. No. 14/990,323, filed Jan. 7, 2016, entitled "SYSTEMS AND METHODS FOR ADAPTIVE LOCAL ALIGNMENT FOR GRAPH GENOMES," the entire contents of which is incorporated herein by reference in its entirety.

FIELD OF THE INVENTION

The invention relates to systems and methods for adaptive local alignment for graph genomes.

BACKGROUND

A person's genetic information has the potential to reveal much about their health and life. A risk of cancer or a genetic disease may be revealed by the sequences of the person's genes, as well as the possibility that his or her children could inherit a genetic disorder. Genetic information can also be used to identify an unknown organism, such as potentially infectious agents discovered in samples from public food or water supplies. Next-generation sequencing (NGS) technologies are available that can sequence entire genomes quickly. Some approaches to analyzing sequence reads involve mapping the sequence reads to a reference genome. Mapping reads to a reference can be done by aligning each read to a relevant portion of the reference.

SUMMARY

The described methods and systems provide a method for automatically analyzing sequence data using a graph, such as a reference directed acyclic graph (DAG), and accounting for the various difficulties (e.g., complexities) of sequence alignment and genomic variation without requiring intermediate input or guidance from a user. Essentially, the described methods and systems simplify and optimize the process for sequence alignment between a sample sequence and a reference genome because the systems and methods function autonomously from the user (after the sequence information is received). A processor can, for example, identify and align the sequence information in a manner that meets a user's requirements for accuracy and expediency. In some cases, the sequence information can be directly transmitted to the systems described herein, which helps to provide a vastly simplified sequence alignment experience for the user.

Representing genomes as graphs, such as directed acyclic graphs (DAGs), is a powerful tool for coping with the complexities of sequence alignment and genomic variation. In contrast to a single linear reference sequence, a DAG can incorporate myriad types of information about genomic variations, such as single nucleotide polymorphisms (SNPs), small insertions and deletions (indels), and larger structural variants (SVs). Each of these variations can be represented by following different branches through the DAG. Additionally, using DAGs can help to increase the probability of identifying small variations near large known structural variants because the presence of the known structural variants in the graph improves the quality of the alignment. Thus, known variations can be reliably accounted for and identified by aligning reads containing the known variations to a sequence path that includes those variations.

However, the complex nature of DAGs can result in a combinatorial explosion when used with conventional linear alignment tools thereby rendering alignment to a DAG computationally expensive and cost prohibitive. The methods and systems described throughout this document can automatically and efficiently analyze sequence data using the reference DAG even when doing so would conventionally be undesirable (e.g., computationally expensive, time consuming, imprecise, and/or cost prohibitive). The systems and methods can analyze the difficulty of aligning the sequence data with the reference DAG based on a predicted alignment difficulty (e.g., due to the DAG complexity, sequence length, total processing time, remaining processing time, or any combination thereof) between the reference DAG and the sequence data. By choosing and employing a selected alignment algorithm based on this predicted alignment difficulty, the methods and systems can efficiently analyze sequence data.

In one aspect of the invention, a method includes identifying, within a graph representing a reference genome, a plurality of candidate mapping positions that relate to the genetic information, the graph including nodes representing genetic sequences and edges connecting pairs of nodes; determining, by means of a computer system, whether an alignment with the graph surrounding each of the plurality of candidate mapping positions is advanced or basic; and performing for each candidate mapping position, by means of the computer system, a local alignment based on whether the local alignment is advanced or basic. The advanced local alignment includes a first-local-alignment algorithm, and the basic local alignment includes a second-local-alignment algorithm. Based on the local alignments, the method further includes identifying the mapped position of the sequence read within the reference genome.

In another aspect of the invention, the system for determining a subject's genetic information, the system includes a computer system comprising a processor coupled to memory and operable to: receive identities of a plurality of nucleotides at known locations on a reference genome; receive sequence reads from a sample from a subject; and map the sequence reads to the reference genome, thereby identifying a corresponding location on the reference genome. The mapping includes identifying, within a graph representing a reference genome, a plurality of candidate mapping positions that relate to the genetic information, the graph comprising nodes representing genetic sequences and edges connecting pairs of nodes; determining, by means of a computer system, whether an alignment with the graph surrounding each of the plurality of candidate mapping positions is advanced or basic; and performing for each candidate mapping position, by means of the computer system, a local alignment based on whether the local alignment is advanced or basic. The advanced local alignment includes a first-local-alignment algorithm, and the basic local alignment includes a second-local-alignment algorithm. Based on the local alignments, the system identifies the mapped position of the sequence read within the reference genome.

Implementations can include one or more of the following features.

In some implementations, the method further includes performing, by means of the computer system, a global alignment for the sequence read based on whether the global alignment is advanced or basic. The advanced global alignment includes a first-global-alignment algorithm, and the basic global alignment includes alignment includes a second-global-alignment algorithm. The global alignment provides information indicative of the plurality of candidate mapping positions.

In certain implementations, the first-local-alignment algorithm is different from the second-local-alignment algorithm.

In some implementations, the first-global-alignment algorithm is different from the second-global-alignment algorithm.

In certain implementations, at least one of the first-local-alignment algorithm and the second-local-alignment algorithm is different from at least one of the first-global-alignment algorithm and the second-global-alignment algorithm.

In some implementations, the method further includes determining whether the local alignment is advanced or basic based at least in part on at least one of: the complexity of the graph, a length of the graph, a total processing time, a remaining processing time, and a number of repeating elements.

In certain implementations, a complex graph includes 10 or more nodes.

In some implementations, a simple graph includes 5 or fewer nodes.

In certain implementations, the first-local-alignment algorithm includes a pattern matching algorithm.

In some implementations, the pattern matching algorithm includes at least one of the following: a Boyer-Moore algorithm, a Horspool algorithm, and a Tarhio-Ukkonen algorithm.

In certain implementations, the second-local-alignment algorithm includes a linear alignment algorithm.

In some implementations, each node and edge stores a list of one or more adjacent objects, and wherein identifying the plurality of candidate mapping positions comprises finding related alignments between the sequence read and the reference genome.

In certain implementations, candidate mapping positions relate to the genetic information if a predetermined alignment quality is met between the candidate mapping position and the sequence read.

In some implementations, the method further includes ranking each of the candidate mapping positions based on the quality of the local alignment.

In certain implementations, each of the plurality of candidate mapping positions defines a selected path through the graph.

In some implementations, the processor is further operable to: perform a global alignment, by means of the computer system, for the sequence read based on whether the global alignment is advanced or basic. The advanced global alignment includes a first-global-alignment algorithm, and the basic global alignment includes a second-global-alignment algorithm. The global alignment provides information indicative of the plurality of candidate mapping positions.

In certain implementations, each node and edge stores a list of one or more adjacent objects, and wherein identifying the plurality of candidate mapping positions comprises finding related alignments between the sequence read and the candidate mapping position.

In some implementations, the complexity of the graph varies with a remaining processing time estimate to reduce a total processing time.

In certain implementations, the first-local-alignment algorithm is different from the second-local-alignment algorithm.

In some implementations, the first-global-alignment algorithm is different from the second-global-alignment algorithm.

In certain implementations, at least one of the first-local-alignment algorithm and the second-local-alignment algorithm is different from at least one of the first-global-alignment algorithm and the second-global-alignment algorithm.

In some implementations, the mapping further includes determining whether the local alignment is advanced or basic based at least in part on at least one of: the complexity of the graph, a length of the graph, a total processing time, a remaining processing time, and a number of repeating elements.

In certain implementations, a complex graph includes 10 or more nodes.

In some implementations, a simple graph includes 5 or fewer nodes.

In certain implementations, the first-local-alignment algorithm includes a pattern matching algorithm.

In some implementations, the pattern matching algorithm includes at least one of the following: a Boyer-Moore algorithm and a Tarhio-Ukkonen algorithm.

In certain implementations, the second-local-alignment algorithm includes a linear alignment algorithm.

In some implementations, the candidate mapping positions relate to the genetic information if a predetermined alignment quality is met between the candidate mapping position and the sequence read.

In certain implementations, the mapping further includes ranking each of the candidate mapping positions based on the quality of the local alignment.

In some implementations, each of the plurality of candidate mapping positions defines a selected path through the graph.

Implementations can include one or more of the following advantages.

Many of the methods described herein can account for the complexity of a reference graph by adjusting the alignment methods based on the complexity. Regions of a reference graph with a large number of nodes will typically result in an exponential number of calculations, which leads to excessive cost and processing time during the alignment process. Other sequence alignment methods, such as the Graph Smith-Waterman algorithm, have been adapted to accommodate this complexity and to work with DAGs (e.g., as disclosed in U.S. Pub. 2015/0057946 and U.S. Pub. 2015/0056613, both incorporated by reference); however, these methods have a high initial computational cost and therefore are not amenable for use with large data sets. By adjusting the alignment methods based on the complexity of the reference DAG, an optimal alignment method can be used. For example, if genomic information is being aligned with a relatively simple reference graph, a linear alignment method can be used to save resources (e.g., time and computational costs). In other cases, if the reference graph is relatively complex, other sequence alignment methods, such as the modified Graph Smith-Waterman algorithm may be an alignment tool well-suited to the task despite the high initial computational costs.

In some implementations, the predicted alignment difficulty can vary during the alignment process. The alignment techniques described herein can continually assess the alignment difficulty and dynamically adapt the alignment tools in response to any changes. For example, two or more alignment tools can be used during the same alignment process.

BRIEF DESCRIPTION OF THE DRAWINGS

FIG. 3 shows the matrices that represent the comparison.

DETAILED DESCRIPTION

In general, the methods and systems described herein relate to determining a subject's genetic information. Information representing at least a portion of the subject's DNA (e.g., a sequence read) is globally aligned with a graph, such as a reference genomic directed acyclic graph (DAG), to identify candidate paths or mapping positions through the genomic DAG. The genomic information can then be compared against the candidate paths with a higher degree of accuracy as compared to the original global alignment. This two-step alignment analysis allows for the selection of an appropriate alignment algorithm based on the alignment difficulty and an acceptable alignment tolerance, thereby reaping considerable computational savings resources because resources are not needlessly expended.

Additionally, the present disclosure recognizes, in certain embodiments, that the problem of combinatorial explosion associated with aligning sequence data to genomic DAGs is solved by an alignment method that analyzes the complexity of a DAG and chooses an alignment algorithm based on the complexity. For example, sequence reads can be quickly aligned to portions of a DAG that have low complexity using a pattern matching algorithm or a linear alignment algorithm. However, for complex portions of the DAG, the number of paths that must be analyzed by a pattern matching or linear alignment algorithm grows exponentially, leading to a corresponding exponential decrease in performance of the pattern matching or linear alignment tool. In these cases, a graph-aware algorithm may be substituted. The graph-aware algorithm may have a high initial overhead cost, but its decrease in performance scales linearly as the complexity of the graph increases, making it a preferred choice for complex regions of a DAG.

The following describes methods for indexing collections of data strings represented in a form of DAGs and performing efficient string search including exact and approximate matching techniques. Among other applications, these methods can be used to quickly and efficiently find genomic data sequences (e.g., reads produced by DNA sequencing machines) in genome graphs representing genome data variations.

Figure 1:
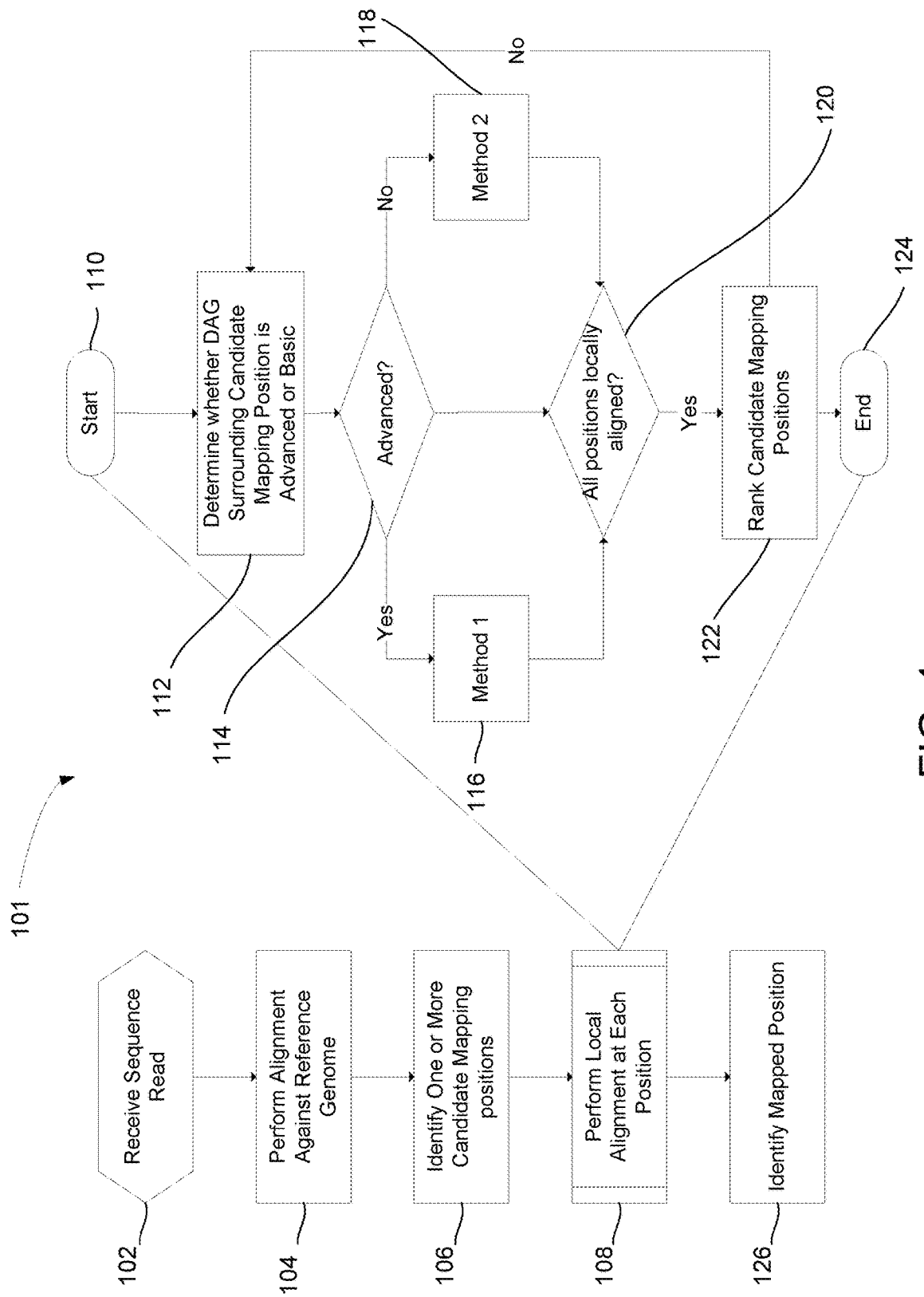
FIG. 1 diagrams a method for aligning sequence reads to a reference genome.

FIG. 1 diagrams a method 101 for analyzing genomic sequence information. At step 102 sequence reads from a sample from a subject are received. Sequence reads can be received from a nucleic acid sequencing instrument, such as an Illumina® HiSeq2500, a Roche 454 GS FLX+, an Ion Torrent PGM™, and the like. A processor coupled to the tangible memory device is used to globally align 104 the sequence read against the reference genome to identify 106 one or more candidate mapping positions. These candidate mapping positions represent acceptable alignments between the received sequence reads and the paths through the reference DAG (e.g., a location within the reference genome that could be related to the sequence read). In some cases, a report can be provided that identifies a one or more of the candidate mapping positions.

Next-generation sequencing and alignment can be computationally expensive. For example, over 900 million paired-end 100 bp sequence reads are needed to obtain 30× coverage of the human genome. As will be described in further detail below, certain algorithms, such as various pattern matching and linear alignment algorithms, scan each sequence read over a reference sequence to identify an exact, optimal, or best-fit match. But this approach is typically computationally infeasible given the scales associated with next-generation sequencing. To solve this problem, a heuristic approach may be used to reduce the total number of computations required. For example, one approach is to separate an alignment into "coarse" and "fine" stages. In the coarse stage, a fast, yet often incomplete or inexact alignment is performed to identify a number of candidate regions to which a particular sequence read aligns. This is referred to as a global alignment or a global search because the read has aligned considering the entirety of the reference sequence. In the second, fine stage, each candidate region is subsequently analyzed using a more computationally expensive, yet exact algorithm. This is referred to as a local alignment or local search because the alignment is restricted to the local space identified during the coarse stage. In certain examples, this may be referred to as a "seed and extend" strategy; the global alignment yields a number of seed positions, which are then extended during the local alignment stage. The candidate positions may then be scored and ranked, yielding the best aligned position for each sequence read.

For example, one approach for performing a global alignment 104 is to place many small sections, or k-mers, of the reference DAG into a computer hash function. The hash function calculates an index as a function of the k-mer. The index identifies an entry in a hash table, and the positions of the k-mer within the reference DAG are stored in that entry, i.e., in the entry indexed by the hash of the k-mer. A sequence read is analyzed by hashing some or all of its k-mers and the corresponding entries of the DAG hash table are accessed to read positions within the DAG where those sequence read k-mers can be found. Sections of the DAG where a threshold number of k-mer positions are found are identified as candidate regions within the represented genomes for alignment or mapping of the sequence read. By the described implementation, a sequence read can be mapped to a large number of "good fit" positions within a reference genome very rapidly.

A sequence read can be quickly mapped to a reference using a global alignment algorithm because hash values can be retrieved rapidly (i.e., without iterating over entries in an array). Since a DAG can store a great amount of genetic variation, a sequence read can be mapped to an appropriate portion of one or more certain genomes from among numerous candidate genomes very rapidly. Since sequence reads can be mapped to biologically relevant reference genomes very rapidly, a patient's genetic information can be discerned, or genetic sequences can be identified quickly even against a background of all genetic variety represented in the system. For example, aligning a patient's sequence reads to a DAG representing variations in cancer genomes (such as those from The Cancer Genome Atlas) can be used to quickly identify particular mutations associated with cancer present in the patient.

Once a plurality of candidate mapping positions has been identified 106 by a global searching algorithm 104, a subsection of the graph at each candidate mapping position is identified. In some examples, the subsection of the graph includes at least the number of base pairs in the sequence read for searching (e.g., 50, 100, 200 bp). However, longer subsections can be preferable for local search. Using longer subsections is particularly advantageous when using paired-end or mate-pair sequence reads, which are pairs of sequence reads describing the 5' and 3' ends of a single DNA molecule, often with an inferred insert size distance of 300-600 (paired-end) or 2,000-5,000 (mate pair) base pairs between the 5' and 3' sequence reads. Accordingly, the portions or subsections of the graph for each of the candidate mapping positions can be a variety of sizes ranging from 50 to even 10,000 base pairs.

The processor can then perform 108 a local alignment for each of the candidate mapping positions. With the candidate mapping positions (e.g., "good fit" positions) identified, a processor can perform 108 a local alignment at each of the candidate mapping positions to narrow the candidate mapping positions to identify one or more mapped positions (e.g., "better fit" or "best fit" positions). A processor can start 110 the local alignment process and then determine 112 whether an alignment with the reference DAG surrounding the candidate mapping positions (e.g., the subset of the reference DAG surrounding a candidate mapping position) is advanced or basic. In some examples, an alignment is advanced if the complexity of the subset of the reference DAG exceeds 5 paths. In other examples, the alignment is considered basic if the complexity of the subset of the reference DAG is 5 paths or less. If the alignment is advanced 114, then the processor can use a first alignment tool implementing a first method 116. If the alignment is not advanced (i.e., basic), then the processor can use a second alignment tool implementing a second method 118. The processor can repeat 120 this process until all candidate mapping positions are locally aligned. The processor can then rank 122 the candidate mapping positions to identify the most likely alignment positions corresponding to the received sequence read before ending 124 the local alignment process. Based on these rankings, the processor can identify 126 the mapped position within an acceptable margin of error.

While the method 101 comprises performing 104 a global alignment against a reference DAG, in certain embodiments, a global alignment may be simply performed against a linear reference sequence. This can be advantageous in certain embodiments where using a linear reference sequence for the global alignment can help improve performance. However, the local alignment 108 may still consider a reference DAG structure. Various embodiments are considered to be within the scope of the disclosure.

Figure 2:
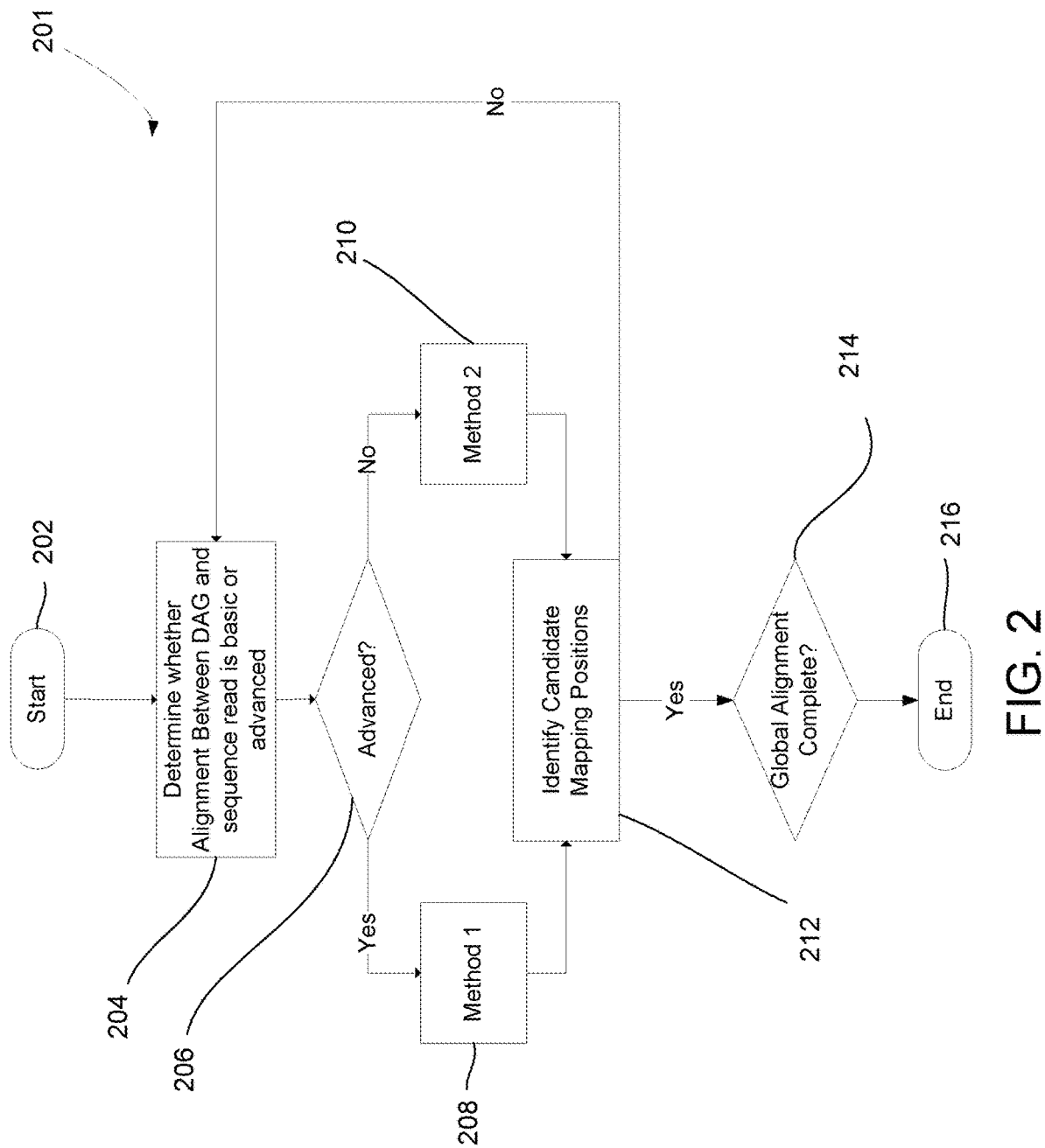
FIG. 2 diagrams a method for performing a global alignment of a sequence read to a reference genome.

In certain embodiments, a global alignment may also consider whether an alignment with the DAG is advanced or basic and select an appropriate algorithm accordingly. FIG. 2 illustrates an exemplary global alignment process 201 for identifying candidate mapping positions for a sequence read. As with the local alignment process 108, the global alignment process 201 can evaluate the reference DAG to determine if the global alignment is advanced or basic. For example, this may be performed in situations wherein the reference DAG is small enough such that pattern matching and linear alignment algorithms may be used for the global alignment stage. For example, a processor can start 202 the local alignment process and then determine 204 whether an alignment with the reference DAG and the sequence read is advanced or basic. In some examples, an alignment is advanced if the complexity of the DAG exceeds 6 paths, as discussed below. In other examples, the alignment is basic if the complexity of the DAG is 6 paths or less. If the alignment is advanced 206, then the processor can use a first alignment tool implementing a first method 208. If the alignment is not advanced (i.e., basic), then the processor can use a second alignment tool implementing a second method 210. The first method 208 and the second method 210 may be the same, different, or partially overlap. In some examples, the first method 208 and/or the second method 210 can correspond to at least one of the first method 116 or the second method 118. Using these alignment tools, the processor can identify 212 the candidate mapping positions. The processor can then repeat this process until the global alignment is complete 214. The processor can then end 216 the global alignment process 201.

If the alignment is basic 118, the second alignment tool may comprise linear alignment methods, such as optimal alignment or pattern matching algorithms. For example, the second alignment tool may comprise an optimal alignment algorithm, such as a Smith-Waterman algorithm, a Needleman-Wunsch algorithm, and the like. These algorithms use a dynamic programming approach in order to find an optimal local alignment between two sequences, but are computationally expensive. To improve performance, pattern matching or string matching algorithms, such as a Boyer-Moore algorithm, a Horspool algorithm, and a Tarhio-Ukkonen algorithm may be used. These algorithms are fast, but typically do not handle variations (such as indels and SNPs) as well as an optimal alignment algorithm. However, pattern matching and string matching algorithms are particularly well suited for aligning sequence reads against graph genomes, such as DAGs. As known variations are already present in the graph, the pattern matching algorithm does not need to consider the presence of indels or other variations within a sequence read; it need only map the sequence read to the most likely branch within the DAG having that variation.

While pattern matching and linear alignment algorithms can function as a fast local alignment tool, each of these methods is easily susceptible to efficiency loss when faced with a high number of comparisons when, for example, a linearized graph genome represents a significant number of combinations. Accordingly, if the alignment is advanced 114, the first alignment tool may comprise a graph-aware or multi-dimensional algorithm, such as Graph Smith-Waterman, as explained in further detail below.

Optimal Alignment Algorithms

Pairwise alignment generally involves placing one sequence along part of target, introducing gaps according to an algorithm, scoring how well the two sequences match, and preferably repeating for various positions along the reference. The best-scoring match is deemed to be the alignment and represents an inference of homology between alignment portions of the sequences. In some embodiments, scoring an alignment of a pair of nucleic acid sequences involves setting values for the probabilities of substitutions and indels. When individual bases are aligned, a match or mismatch contributes to the alignment score by a substitution score, which could be, for example, 1 for a match and −0.33 for a mismatch. An indel deducts from an alignment score by a gap penalty, which could be, for example, −1. Gap penalties and substitution probabilities can be based on empirical knowledge or a priori assumptions about how sequences evolve. Their values affect the resulting alignment. Particularly, the relationship between the gap penalties and substitution probabilities influences whether substitutions or indels will be favored in the resulting alignment.

Stated formally, an alignment represents an inferred relationship between two sequences, x and y. For example, in some embodiments, an alignment A of sequences x and y maps x and y respectively to another two strings x' and y' that may contain spaces such that: (i) |x'|=|y'|; (ii) removing spaces from x' and y' should get back x and y, respectively; and (iii) for any i, x'[i] and y'[i] cannot be both spaces.

A gap is a maximal substring of contiguous spaces in either x' or y'. An alignment A can include the following three kinds of regions: (i) matched pair (e.g., x'[i]=y'[i]; (ii) mismatched pair, (e.g., x'≠y'[i] and both are not spaces); or (iii) gap (e.g., either x'[i . . . j] or y'[i . . . j] is a gap). In certain embodiments, only a matched pair has a high positive score a. In some embodiments, a mismatched pair generally has a negative score b and a gap of length r also has a negative score g+rs where g, s<0. For DNA, one common scoring scheme (e.g. used by BLAST) makes score a=1, score b=−3, g=−5 and s=−2. The score of the alignment A is the sum of the scores for all matched pairs, mismatched pairs and gaps. The alignment score of x and y can be defined as the maximum score among all possible alignments of x and y.

Any pair may have a score a defined by a 4×4 matrix B of substitution probabilities. For example, B(i,i)=1 and 0<B(i,j)<1 [for i≠j], is one possible scoring system. For instance, where a transition is thought to be more biologically probable than a transversion, matrix B could include B(C,T)=0.7 and B(A,T)=0.3, or other values desired or determined by methods known in the art.

A pairwise alignment, generally, involves—for sequence Q (query) having m characters and a reference genome T (target) of n characters—finding and evaluating possible local alignments between Q and T. For any 1≤i≤n and 1≤j≤m, the largest possible alignment score of T[h . . . i] and Q[k . . . j], where h≤i and k≤j, is computed (i.e. the best alignment score of any substring of T ending at position i and any substring of Q ending at position j). This can include examining all substrings with cm characters, where c is a constant depending on a similarity model, and aligning each substring separately with Q. Each alignment is scored, and the alignment with the preferred score is accepted as the alignment. One of skill in the art will appreciate that there are exact and approximate algorithms for sequence alignment. Exact algorithms will find the highest scoring alignment, but can be computationally expensive. Two well-known exact algorithms are Needleman-Wunsch (J Mol Biol, 48(3):443-453, 1970) and Smith-Waterman (J Mol Biol, 147(1):195-197, 1981; Adv. in Math. 20(3), 367-387, 1976). A further improvement to Smith-Waterman by Gotoh (J Mol Biol, 162(3), 705-708, 1982) reduces the calculation time from $O(m^2n)$ to $O(mn)$ where m and n are the sequence sizes being compared and is more amenable to parallel processing. In the field of bioinformatics, it is Gotoh's modified algorithm that is often referred to as the Smith-Waterman algorithm. Smith-Waterman approaches are being used to align larger sequence sets against larger reference sequences as parallel computing resources become more widely and cheaply available. See, e.g., Amazon's cloud computing resources. All of the journal articles referenced herein are incorporated by reference in their entireties.

The original Smith-Waterman (SW) algorithm is a linear alignment algorithm that aligns linear sequences by rewarding overlap between bases in the sequences, and penalizing gaps between the sequences. Smith-Waterman also differs from Needleman-Wunsch, in that SW does not require the shorter sequence to span the string of letters describing the longer sequence. That is, SW does not assume that one sequence is a read of the entirety of the other sequence. Furthermore, because SW is not obligated to find an alignment that stretches across the entire length of the strings, a local alignment can begin and end anywhere within the two sequences.

The original SW algorithm is expressed for an n×m matrix H, representing the two strings of length n and m, in terms of equation (1):

$$H\_k0 = H\_01 = 0 \text{ (for } 0 \leq k \leq n \text{ and } 0 \leq l \leq m)$$

$$H\_ij = \max\{H\_(i-1,j-1) + s(a\_i, b\_j), H\_(i-1,j) - W\_in, H\_(i,j-1) - W\_del, 0\} \text{ (for } 1 \leq i \leq n \text{ and } 1 \leq j \leq m) \quad (1)$$

In the equations above, s(ai,bj) represents either a match bonus (when ai=bj) or a mismatch penalty (when ai≠bj), and insertions and deletions are given the penalties Win and Wdel, respectively. In most instances, the resulting matrix has many elements that are zero. This representation makes it easier to backtrace from high-to-low, right-to-left in the matrix, thus identifying the alignment.

Once the matrix has been fully populated with scores, the SW algorithm performs a backtrack to determine the alignment. Starting with the maximum value in the matrix, the algorithm will backtrack based on which of the three values (Hi−1,j−1, Hi−1,j, or Hi,j−1) was used to compute the final maximum value for each cell. The backtracking stops when a zero is reached. The optimal-scoring alignment may contain greater than the minimum possible number of insertions and deletions, while containing far fewer than the maximum possible number of substitutions.

SW or SW-Gotoh may be implemented using dynamic programming to perform local sequence alignment of the two strings, S and A, of sizes m and n, respectively. This dynamic programming employs tables or matrices to preserve match scores and avoid re-computation for successive cells. Each element of the string can be indexed with respect to a letter of the sequence, that is, if S is the string ATCGAA, S[1]=A.

Instead of representing the optimum alignment as Hi,j (above), the optimum alignment can be represented as B[j,k] in equation (2) below:

$$B[j,k] = \max(p[j,k], i[j,k], d[j,k], 0) \text{ (for } 0 \leq j \leq m, 0 < k \leq n) \quad (2)$$

The arguments of the maximum function, B[j,k], are outlined in equations (3)-(5) below, wherein MISMATCH_PEN, MATCH_BONUS, INSERTION_PEN, DELETION_PEN, and OPENING_PEN are all constants, and all negative except for MATCH_BONUS (PEN is short for PENALTY). The match argument, p[j,k], is given by equation (3), below:

$$p[j,k] = \max(p[j-1,k-1], i[j-1,k-1], d[j-1,k-1]) + \text{MISMATCH\_PEN, if } S[j]A[k] = \max(p[j-1,k-1], i[j-1,k-1], d[j-1,k-1]) + \text{MATCH\_BONUS, if } S[j] = A[k] \quad (3)$$

the insertion argument i[j,k], is given by equation (4), below:

$$i[j,k]=\max(p[j-1,k]+\text{OPENING\_PEN}, i[j-1,k], d[j-1,k]+\text{OPENING\_PEN})+\text{INSERTION\_PEN} \quad (4)$$

and the deletion argument d[j,k], is given by equation (5), below:

$$d[j,k]=\max(p[j,k-1]+\text{OPENING\_PEN}, i[j,k-1]+\text{OPENING\_PEN}, d[j,k-1])+\text{DELETION\_PEN} \quad (5)$$

For all three arguments, the [0,0] element is set to zero to assure that the backtrack goes to completion, i.e., p[0,0]=i[0,0]=d[0,0]=0.

The scoring parameters are somewhat arbitrary, and can be adjusted to achieve the behavior of the computations. One example of the scoring parameter settings (Huang, Chapter 3: Bio-Sequence Comparison and Alignment, ser. Curr Top Comp Mol Biol. Cambridge, Mass.: The MIT Press, 2002) for DNA would be:
MATCH_BONUS: 10
MISMATCH_PEN: −20
INSERTION_PEN: −40
OPENING_PEN: −10
DELETION_PEN: −5

The relationship between the gap penalties (INSERTION_PEN, OPENING_PEN) above help limit the number of gap openings, i.e., favor grouping gaps together, by setting the gap insertion penalty higher than the gap opening cost. Of course, alternative relationships between MISMATCH_PEN, MATCH_BONUS, INSERTION_PEN, OPENING_PEN and DELETION_PEN are possible.

Smith-Waterman and Needleman-Wunsch are exact alignment algorithms and identify optimal alignments, including those with short insertions and deletions. However, it can be as computationally expensive as naïve pattern matching algorithms, and has a processing time typically on the order of O(mn). As a result, the use of the Smith-Waterman algorithm is primarily reserved for local alignment. However, when applied to a multi-dimensional data structure such as a reference DAG, these algorithms can take an excessive amount of time to complete. In these cases, more efficient pattern matching algorithms may be substituted.

Pattern Matching Algorithms

Pattern matching algorithms use mathematical techniques to reduce the total number of pairwise comparisons in order to improve efficiency. In a short read alignment, a short read P having n nucleotides is aligned with the left-most portion of a reference sequence T, creating a window of length n. After a match or mismatch determination, the window is shifted to the right for additional comparisons. Pattern matching algorithms increase local alignment efficiency by shifting the window farther to the right that a single character, i.e., by skipping a certain number of comparisons which would result in a mismatch. In particular, some pattern matching algorithms process a sequence read, or pattern, in order to create a "shift table" that indicates how many comparisons can safely be skipped depending on the mapping of the short read at the current position.

To create a shift table, many pattern matching algorithms operate in two phases: a pre-processing phase and a search phase. The pre-processing phase typically processes the pattern itself to generate information that can aid the search phase by providing a table of shift values after each comparison. Improvement in efficiency of a search can be achieved by altering the order in which the characters are compared at each attempt, and by choosing a shift value that permits the skipping of a predefined number of characters in the text after each attempt. The search phase then uses this information to ignore certain character comparisons, reducing the total number of comparisons and thus the overall execution time.

The Boyer-Moore algorithm is one of the most efficient. See Boyer, R. S., Moore, J. S., "A Fast String Searching Algorithm", Comm. ACM 20(10), 762-772. Boyer-Moore preprocesses a pattern to create two tables: a Boyer-Moore bad character (bmBc) table and a Boyer-Moore good suffix (bmGs) table. For each character in the alphabet (e.g., "A", "C", "G", and "T", representing the four possible nucleotides), the bad character table stores a shift value based on the occurrence of the character in the pattern (i.e., short read). The good-suffix table stores the matching shift value for each character in the read. The maximum of the shift value in either table is considered after each comparison during a search, which is then used to advance the window. Boyer-Moore does not allow any mismatches between the read and the reference sequence, and thus is a perfect-match search algorithm.

Boyer-Moore serves as the basis for several pattern matching algorithms that can be used for sequence alignment. One variation of Boyer-Moore is the Horspool algorithm. See Horspool, R. N., "Practical Fast Searching in Strings", Software—Practice & Experience, 10, 501-506. Horspool simplifies Boyer-Moore by recognizing that the bad-character shift of the right-most character of the window can be sufficient to compute the value of the shift. These shift values are then determined in the pre-processing stage for all of the characters in the alphabet, i.e., the possible nucleotides. Horspool is particularly efficient in practical situations when the length of the pattern is small, such as for sequence reads generated by next-generation sequencing. Like Boyer-Moore, Horspool is a perfect-match search algorithm.

Another variation of Boyer-Moore that allows for a certain number of mismatches is the Tarhio-Ukkonen algorithm. See Tarhio, J., Ukkonen, E., "Approximate Boyer-Moore String Matching", SIAM J. Comput., 22, 243-260. Because it allows for mismatches, Tarhio-Ukkonen can be used to provide approximate alignments for next generation sequencing reads to a reference sequence. During a pre-processing phase, Tarhio-Ukkonen calculates shift values for every character that take into account a desired allowable number of mismatches, k. Tarhio-Ukkonen is able to identify matches in expected time $$\left(kn\left(\frac{1}{m-k}+\frac{k}{c}\right)\right),$$

where c is the size of the alphabet. The use of approximation in pattern matching algorithms such as Tarhio-Ukkonen is particularly useful for next generation sequencing alignments due to inherent noise present in sequence reads generated by most next generation sequencing technologies. Furthermore, because the primary goal of most genomic sequence analyses is to identify unknown variations (primarily, SNPs) that may be present in a sample, approximate pattern matching algorithms help to identify novel polymorphisms in sequence data. In contrast, the Boyer-Moore and Horspool algorithms would reject such reads if there were any differences between the read and the reference.

When used for next generation sequencing alignment, pattern matching algorithms can be used as a fast local alignment tool. In particular, pattern matching algorithms typically have performance that exceeds that of traditional local alignment algorithms for sequence data, such as Needleman-Wunsch and Smith-Waterman. However, when applied to a graph genome, combinatorial complexity can quickly increase the number of comparisons to a point in which improvements in efficiency are lost. In other words, for a local alignment to a subset of a reference DAG, the expected time for the Boyer-Moore family is multiplied by the number of linearized paths. Additionally, despite variants that are able to address mismatches and small insertions and deletions, the Boyer-Moore family of algorithms do not perform particularly well when handling alignments involving novel variations (that are not already present in the graph). Exact alignment algorithms, such as Needleman-Wunsch and Smith-Waterman are able to accurately identify variations; however, these algorithms run in O(mn) time and similarly suffer from combinatorial explosion when applied to a DAG.

One solution to this problem is to use a multi-dimensional or graph-aware algorithm, such as if the alignment is advanced. One example of a graph-aware alignment algorithm is a modified Smith-Waterman algorithm that considers the highest scoring paths through a DAG ("Graph Smith Waterman"). Like Smith-Waterman, Graph Smith-Waterman is an exact alignment algorithm and thus is able to identify optimal local alignments that include insertions and deletions. However, when applied to a linear reference or a DAG having low complexity, Graph Smith-Waterman can be slow relative to the alignment speed of a pattern matching algorithm.

Graph-Aware Alignment Algorithms

Certain alignment algorithms have been developed that are able to provide accurate and relatively fast local alignments when used with DAGs or other graph data structures. For example, a Graph Smith-Waterman algorithm as described below calculates a Smith-Waterman score matrix between the sequence read and each node in a DAG, such that the maximum scores are propagated across the matrices for each node. In this way, the linear portions of the DAG with the highest scores in relation to the sequence read are serialized and chained together. One need only look back through the chained Smith-Waterman matrices to identify both the optimal alignment and path of the DAG.

Figure 3:
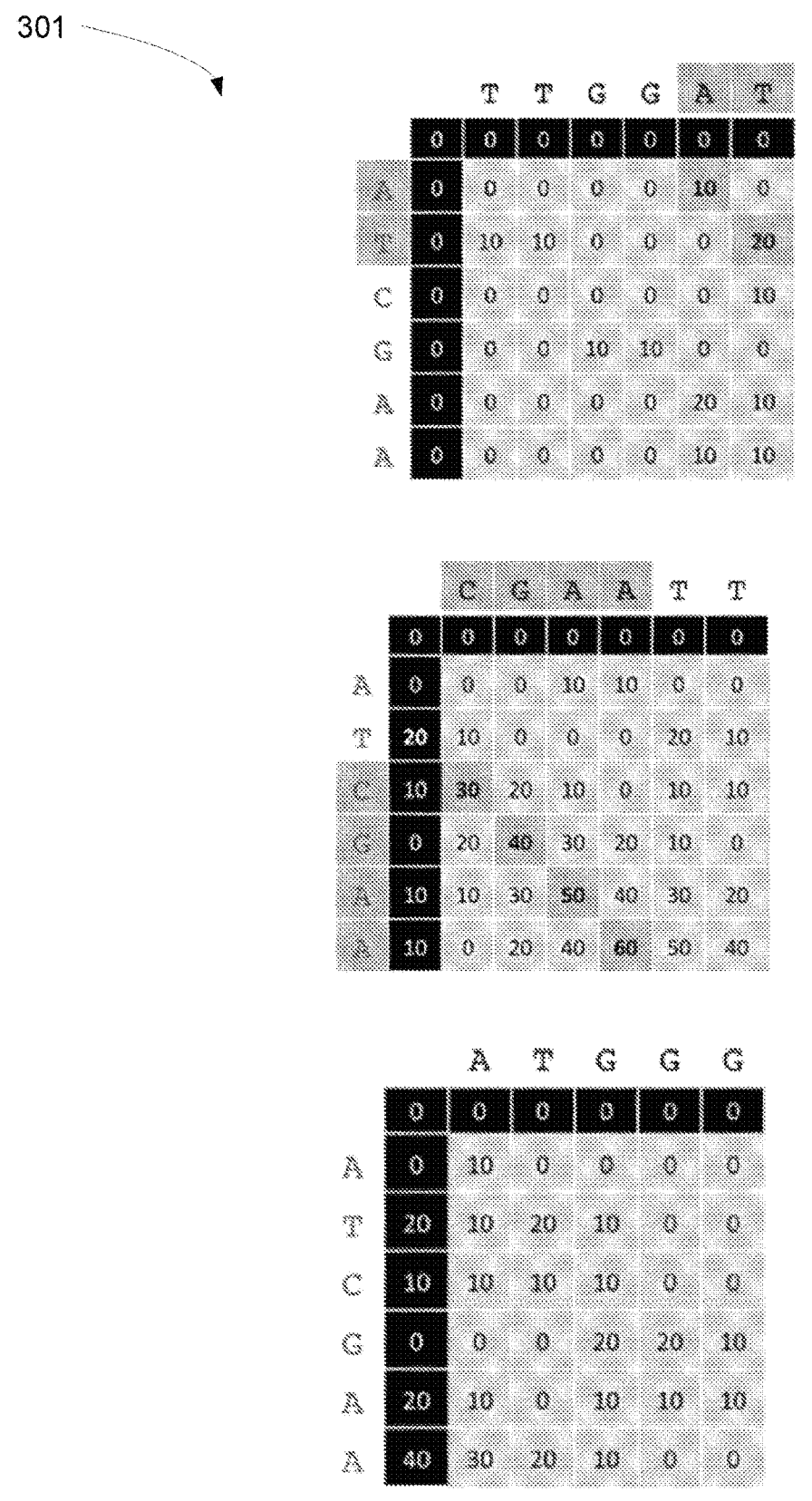

In some embodiments, the methods and systems of the invention use a modified Smith-Waterman operation that involves a multi-dimensional look-back through the reference DAG (such as the reference DAG 331 of FIG. 3). Multi-dimensional operations of the invention provide for a "look-back" type analysis of sequence information (as in Smith-Waterman), wherein the look back is conducted through a multi-dimensional space that includes multiple pathways and multiple nodes. The multi-dimensional algorithm can be used to align sequence reads against the graph-type reference. That alignment algorithm identifies the maximum value for $C_{i,j}$ by identifying the maximum score with respect to each sequence contained at a position on the graph. In fact, by looking "backwards" at the preceding positions, it is possible to identify the optimum alignment across a plurality of possible paths.

The modified Smith-Waterman operation described here, aka the multi-dimensional alignment, provides exceptional speed when performed in a genomic graph system that employs physical memory addressing (e.g., through the use of native pointers or index free adjacency as discussed above). The combination of multi-dimensional alignment to the graph of reference DAG 331 with the use of spatial memory addresses (e.g., native pointers or index-free adjacency) improves what the computer system is capable of, facilitating whole genomic scale analysis to be performed using the methods described herein.

The operation includes aligning a sequence, or string, to a graph. For the purpose of defining the algorithm, let S be the string being aligned, and let D be the directed graph to which S is being aligned. The elements of the string, S, are bracketed with indices beginning at 1. Thus, if S is the string ATCGAA, S[1]=A, S[4]=G, etc.

In certain embodiments, for the graph, each letter of the sequence of a node will be represented as a separate element, d. In a preferred embodiment, node or edge objects contain the sequences and the sequences are stored as the longest-possible string in each object. A predecessor of d is defined as:

(i) If d is not the first letter of the sequence of its object, the letter preceding d in its object is its (only) predecessor;

(ii) If d is the first letter of the sequence of its object, the last letter of the sequence of any object that is a parent of d's object is a predecessor of d.

The set of all predecessors is, in turn, represented as P[d].

In order to find the "best" alignment, the algorithm seeks the value of M[j,d], the score of the optimal alignment of the first j elements of S with the portion of the graph preceding (and including) d. This step is similar to finding $H_{i,j}$ in equation 1 above. Specifically, determining M[j,d] involves finding the maximum of a, i, e, and 0, as defined below:

$$M[j,d]=\max\{a,i,e,0\} \qquad (6)$$

where e=max{M[j, p*]+DELETE_PEN} for p* in P[d]
i=M[j−1, d]+INSERT_PEN
a=max{M[j−1, p*]+MATCH_SCORE} for p* in P[d], if S[j]=d;
   max{M[j−1, p*]+MISMATCH_PEN} for p* in P[d], if S[j]≠d As described above, e is the highest of the alignments of the first j characters of S with the portions of the graph up to, but not including, d, plus an additional DELETE_PEN. Accordingly, if d is not the first letter of the sequence of the object, then there is only one predecessor, p, and the alignment score of the first j characters of S with the graph (up-to-and-including p) is equivalent to M[j,p]+DELETE_PEN. In the instance where d is the first letter of the sequence of its object, there can be multiple possible predecessors, and because the DELETE_PEN is constant, maximizing [M[j, p*]+DELETE_PEN] is the same as choosing the predecessor with the highest alignment score with the first j characters of S.

In equation (6), i is the alignment of the first j−1 characters of the string S with the graph up-to-and-including d, plus an INSERT_PEN, which is similar to the definition of the insertion argument in SW (see equation 1).

Additionally, a is the highest of the alignments of the first j characters of S with the portions of the graph up to, but not including, d, plus either a MATCH_SCORE (if the jth character of S is the same as the character d) or a MISMATCH_PEN (if the jth character of S is not the same as the character d). As with e, this means that if d is not the first letter of the sequence of its object, then there is only one predecessor, i.e., p. That means a is the alignment score of the first j−1 characters of S with the graph (up-to-and-including p), i.e., M[j−1,p], with either a MISMATCH_PEN or MATCH_SCORE added, depending upon whether d and the jth character of S match. In the instance where d is the first letter of the sequence of its object, there can be multiple possible predecessors. In this case, maximizing {M[j, p*]+ MISMATCH_PEN or MATCH_SCORE} is the same as choosing the predecessor with the highest alignment score with the first j−1 characters of S (i.e., the highest of the candidate M[j−1,p*] arguments) and adding either a MISMATCH_PEN or a MATCH_SCORE depending on whether d and the jth character of S match.

Again, as in the SW algorithm, the penalties, e.g., DELETE_PEN, INSERT_PEN, MATCH_SCORE and MISMATCH_PEN, can be adjusted to encourage alignment with fewer gaps, etc.

As described in the equations above, the operation finds the optimal (e.g., maximum) value for a sequence read 103 to the reference DAG 331 by calculating not only the insertion, deletion, and match scores for that element, but looking backward (against the direction of the graph) to any prior nodes on the graph to find a maximum score.

Figure 4:
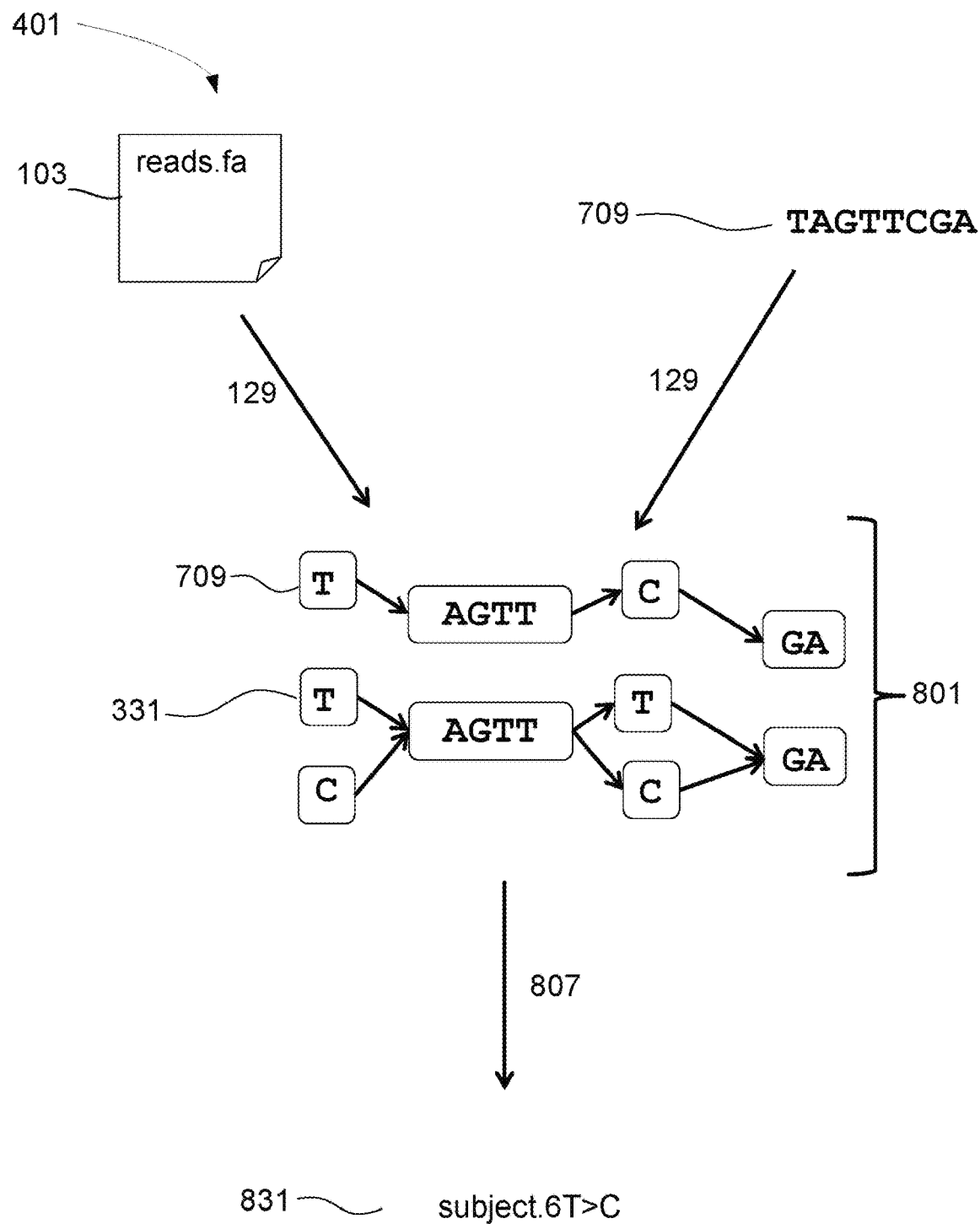
FIG. 4 illustrates finding alignments between a sequence and a reference DAG.

FIG. 3 shows matrices 301 that represent the comparison. The modified Smith-Waterman operation of the invention identifies the highest score and performs a backtrack to identify the proper alignment of the sequence. See, e.g., U.S. Pub. 2015/0057946 and U.S. Pub. 2015/0056613, both incorporated by reference. Systems and methods of the invention can be used to provide a report that identifies a modified base at the position within the genome of the subject. Other information may be found in Kehr et al., 2014, Genome alignment with graph data structures: a comparison, BMC Bioinformatics 15:99 and Lee, 2003, Generating consensus sequences from partial order multiple sequence alignment graphs, Bioinformatics 19(8):999-1008, both incorporated by reference. Thus, identifying an alignment for the genomic information from the sample (e.g., the sequence read 103 of the embodiment of FIG. 4) may include aligning 129 (e.g., using the global alignment 106 or the local alignment 108) one or more of the sequence reads 103 to the reference DAG 331, as shown in FIG. 4. The branches to which the sequence reads 103 have been aligned are identified, along with the corresponding regions within the reference genome.

Graph Smith-Waterman is able to achieve similar computational speed as Smith-Waterman, yet does not suffer from the combinatorial explosion associated with linearizing complex regions of DAGs. In contrast, the performance of Graph Smith-Waterman scales linearly as the complexity of the DAG increases. Additionally, like Smith-Waterman, Graph Smith-Waterman is an exact alignment algorithm and thus is able to identify optimal local alignments that include insertions and deletions. However, when applied to a linear reference sequence or a DAG having low complexity, Graph Smith-Waterman can be slow compared to pattern matching algorithms.

FIG. 4 illustrates finding 129 alignments 401 between the sequence 103 (or a consensus sequence representing an assembly or one or more sequence reads 103) and the reference DAG 331. Alignments can be performed directly against the DAG using the Graph Smith-Waterman algorithm, for example; however, as will be discussed below, alignments may also be performed against the DAG using linear alignment or pattern matching algorithms by first linearizing the DAG.

FIG. 4 also illustrates an optional variant calling 807 step to identify a subject genotype 831. Using alignment operations of the invention, reads can be rapidly mapped to the reference DAG 331 despite their large numbers or short lengths. Numerous benefits obtain by using a graph as a reference. For example, aligning against a graph is more accurate than aligning against a linear reference and then attempting to adjust one's results in light of other extrinsic information. This is primarily because the latter approach enforces an unnatural asymmetry between the sequence used in the initial alignment and other information. Aligning against an object that potentially represents all the relevant physical possibilities is much more computationally efficient than attempting to align against a linear sequence for each physical possibility (the number of such possibilities will generally be exponential in the number of junctions).

Many implementations provide methods that rely on a directed acyclic data structure with the data in an annotated transcriptome. In such a data structure, features (e.g., exons and introns) from the annotated transcriptome are represented as nodes, which are connected by edges. An isoform from the real-world transcriptome is thus represented by a corresponding path through the DAG-based data structure.

Aspects of the described methods relate to the creation or use of a DAG that includes features such as introns and exons from one or more known references. A DAG is understood in the art to refer to data that can be presented as a graph as well as to a graph that presents that data. The DAG can be stored as data that can be read by a computer system for bioinformatic processing or for presentation as a graph. A DAG can be saved in any suitable format including, for example, a list of nodes and edges, a matrix or a table representing a matrix, an array of arrays or similar variable structure representing a matrix, in a language built with syntax for graphs, in a general markup language purposed for a graph, or others. Further, while the DAG is a directed acyclic data structure, in certain embodiments, a reference graph may lack direction or not be acyclic. Various embodiments are considered to be within the scope of the disclosure.

DAG Representation and Storage

Figure 5:
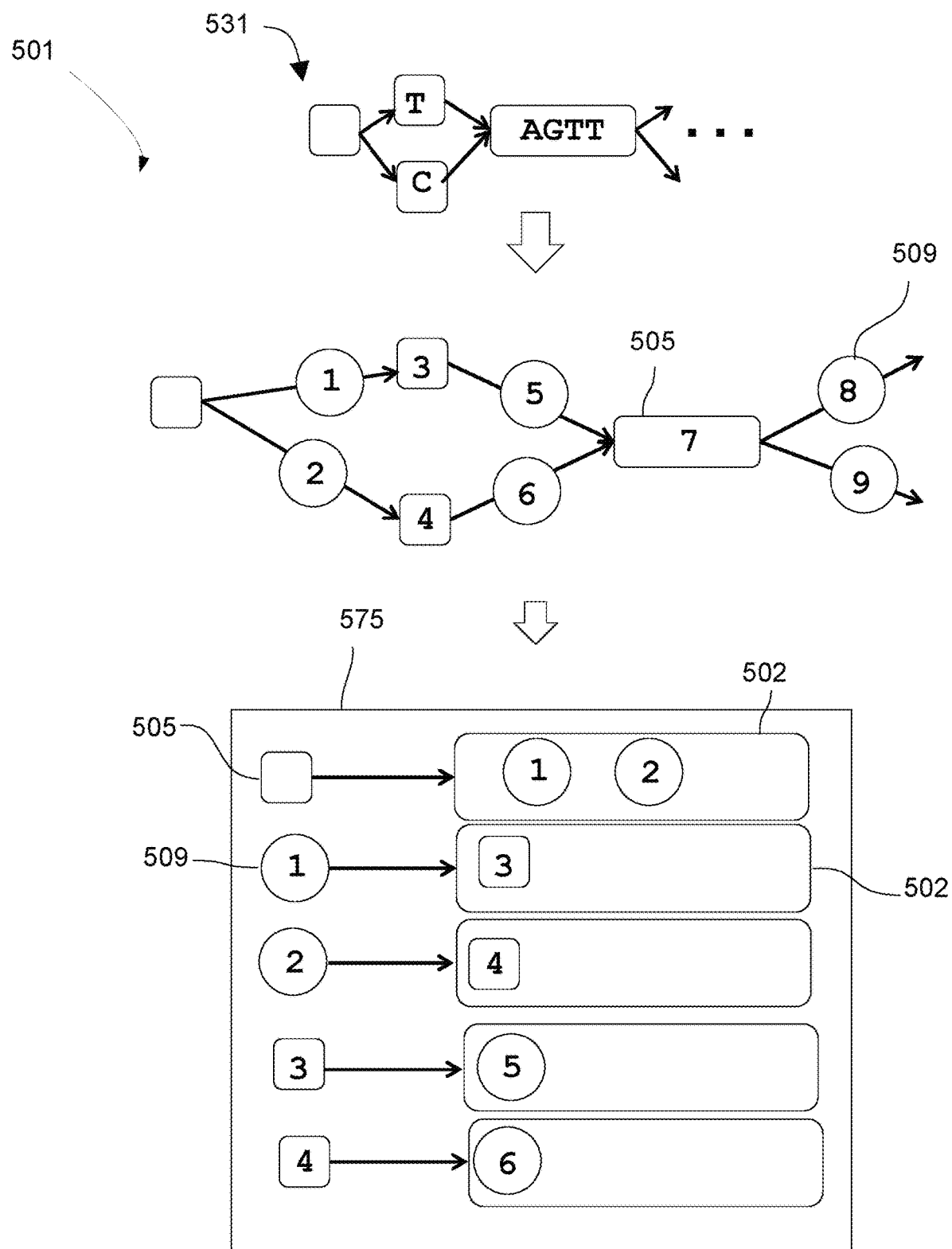
FIG. 5 shows the use of an adjacency list for each vertex and edge in a DAG.

FIG. 5 shows the use of an adjacency list 502 for each vertex 505 and edge 509. A computer system 901 (shown in FIG. 10) creates the reference DAG 531 using an adjacency list 502 for each vertex and edge, wherein the adjacency list 502 for a vertex 505 or edge 509 lists the edges or vertices to which that vertex or edge is adjacent. Each entry in adjacency list 502 is a pointer to the adjacent vertex or edge.

Preferably, each pointer identifies a physical location in the memory subsystem at which the adjacent object is stored. In the preferred embodiments, the pointer or native pointer is manipulatable as a memory address in that it points to a physical location on the memory and permits access to the intended data by means of pointer dereference. That is, a pointer is a reference to a datum stored somewhere in memory; to obtain that datum is to dereference the pointer. The feature that separates pointers from other kinds of reference is that a pointer's value is interpreted as a memory address, at a low-level or hardware level. The speed and efficiency of the described graph genome engine allows a sequence to be queried against a large-scale genomic reference graph (e.g., the reference DAG 531) representing millions or billions of bases, using the computer system 901. Such a graph representation provides means for fast random access, modification, and data retrieval.

In some embodiments, fast random access is supported and graph object storage are implemented with index-free adjacency in that every element contains a direct pointer to its adjacent elements (e.g., as described in U.S. Pub. 2014/0280360 and U.S. Pub. 2014/0278590, each incorporated by reference), which obviates the need for index look-ups, allowing traversals (e.g., as done in the modified SW alignment operation described herein) to be very rapid. Index-free adjacency is another example of low-level, or hardware-level, memory referencing for data retrieval (as required in alignment and as particularly pays off in terms of speed gains in the modified, multi-dimensional Smith-Waterman alignment described below). Specifically, index-free adjacency can be implemented such that the pointers contained within elements are references to a physical location in memory.

Since a technological implementation that uses physical memory addressing such as native pointers can access and use data in such a lightweight fashion without the requirement of separate index tables or other intervening lookup steps, the capabilities of a given computer, e.g., any modern consumer-grade desktop computer, are extended to allow for full operation of a genomic-scale graph (i.e., the reference DAG 531 as a graph that represents all loci in a substantial portion of the reference genome). Thus storing graph elements (e.g., nodes and edges) using a library of objects with native pointers or other implementation that provides index-free adjacency actually improves the ability of the technology to provide storage, retrieval, and alignment for genomic information since it uses the physical memory of a computer in a particular way.

While no specific format is required for storage of a graph, FIG. 5 is presented to illustrate a useful format. With reference back to FIG. 1, it is noted that methods of the invention use the stored graph (e.g., the reference genome) with sequence reads that are obtained from a subject. In some embodiments, sequence reads or obtained as an electronic article, e.g., uploaded, emailed, or FTP transferred from a lab to the computer system 901. In certain embodiments, sequence reads are obtained by sequencing.

In some embodiments, a DAG is stored as a list of nodes and edges. One such way is to create a text file that includes all nodes, with an ID assigned to each node, and all edges, each with the node ID of starting and ending node. Thus, for example, were a DAG to be created for two sentences, "See Jane run," and "Run, Jane run,", a case-insensitive text file could be created. Any suitable format could be used. For example, the text file could include comma-separated values. Naming this DAG "Jane" for future reference, in this format, the DAG "Jane" may read as follows: 1 see, 2 run, 3 jane, 4 run, 1-3, 2-3, 3-4. One of skill in the art will appreciate that this structure is applicable to the introns and exons represented in FIGS. 7 and 8, and the accompanying discussion below.

In certain embodiments, a DAG is stored as a table representing a matrix (or an array of arrays or similar variable structure representing a matrix) in which the (i,j) entry in the N×N matrix denotes that node i and node j are connected (where N is a vector containing the nodes in genomic order). For the DAG to be acyclic simply requires that all non-zero entries be above the diagonal (assuming nodes are represented in genomic order). In a binary case, a 0 entry represents that no edge is exists from node i to node j, and a 1 entry represents an edge from i to j. One of skill in the art will appreciate that a matrix structure allows values other than 0 to 1 to be associated with an edge. For example, any entry may be a numerical value indicating a weight, or a number of times used, reflecting some natural quality of observed data in the world. A matrix can be written to a text file as a table or a linear series of rows (e.g., row 1 first, followed by a separator, etc.), thus providing a simple serialization structure.

Embodiments of the invention include storing a DAG in a language built with syntax for graphs. For example, The DOT Language provided with the graph visualization software packages known as Graphviz provides a data structure that can be used to store a DAG with auxiliary information and that can be converted into graphic file formats using a number of tools available from the Graphviz web site. Graphviz is open source graph visualization software. Graph visualization is a way of representing structural information as diagrams of abstract graphs and networks. It has applications in networking, bioinformatics, software engineering, database and web design, machine learning, and in visual interfaces for other technical domains. The Graphviz layout programs take descriptions of graphs in a simple text language, and make diagrams in useful formats, such as images and SVG for web pages; PDF or Postscript for inclusion in other documents; or display in an interactive graph browser.

In related embodiments, a DAG is stored in a general markup language purposed for a graph, or others. Following the descriptions of a linear text file, or a comma-separated matrix, above, one of skill in the art will recognize that a language such as XML can be used (extended) to create labels (markup) defining nodes and their headers or IDs, edges, weights, etc. However a DAG is structured and stored, embodiments of the invention involve using nodes to represent features such as exons and introns. This provides a useful tool for analyzing sequence reads and discovering, identifying, and representing isoforms.

If nodes represent features or fragments of features, then isoforms can be represented by paths through those fragments. An exon's being "skipped" is represented by an edge connecting some previous exon to some later one. Presented herein are techniques for constructing a DAG to represent alternative splicing or isoforms of genes. Alternative splicing is discussed in Lee and Wang, 2005, Bioinformatics analysis of alternative splicing, Brief Bioinf 6(1):23-33; Heber, et al., 2002, Splicing graphs and EST assembly problems, Bioinformatics 18Suppl:s181-188; Leipzig, et al., 2004, The alternative splicing gallery (ASG): Bridging the gap between genome and transcriptome, Nucl Ac Res 23(13):3977-2983; and LeGault and Dewey, 2013, Inference of alternative splicing from RNA-Seq data with probabilistic splice graphs, Bioinformatics 29(18):2300-2310, the contents of each of which are incorporated by reference. Additional discussion may be found in Florea, et al., 2005, Gene and alternative splicing annotation with AIR, Genome Research 15:54-66; Kim, et al., 2005, ECgene: Genome-based EST clustering and gene modeling for alternative splicing, Genome Research 15:566-576; and Xing, et al., 2006, An expectation-maximization algorithm for probabilistic reconstructions of full-length isoforms from splice graphs, Nucleic Acids Research, 34, 3150-3160, the contents of each of which are incorporated by reference.

Linearizing a DAG for a Linear Alignment Tool

Figure 6:
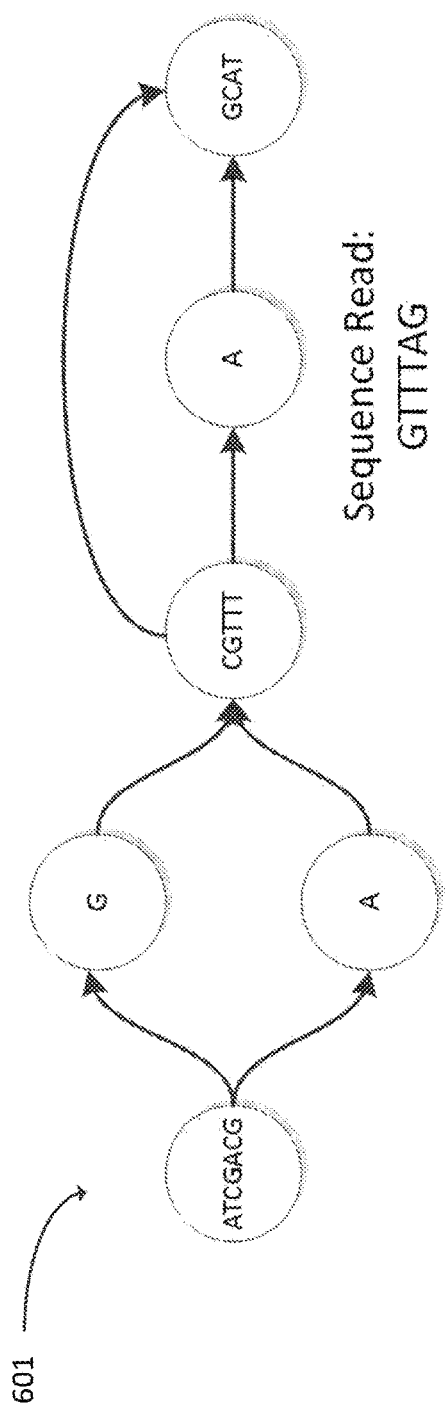
FIG. 6 shows an exemplary DAG and sequence read.

As previously noted, a DAG is a multi-dimensional structure and not immediately amenable to alignment with a linear alignment tool. To use an optimal alignment algorithm or pattern matching algorithm, a reference DAG can be linearized into a format appropriate for the algorithm. In certain embodiments, this can be performed by enumerating each of the possible paths in the subsection of a reference DAG. FIG. 6 illustrates an exemplary DAG 601 representing a subsection of the reference DAG for a candidate mapping position (e.g., a local alignment position). To use a linear alignment algorithm with such a DAG, a depth-first search can be performed by starting at the first node and taking the left-most path. Once the end of the graph is reached, the search returns to the previous node with an untaken path and attempts to take the left-most path again. Each path is associated with a sequence represented by the nodes and edges in the path. The sequence read can then be compared against each of the paths. For example, a depth-first search would identify the following paths and associated sequences from the subsection of the DAG 661 shown in the embodiment of FIG. 6:

```
                                            (SEQ ID NO: 1)
1. ATCGACGGCGTTTGCAT (insertion of A at pos. 13)
                                            (SEQ ID NO: 2)
2. ATCGACGGCGTTTAGCAT (G->A polymorphism at pos. 8)
                                            (SEQ ID NO: 3)
3. ATCGACGACGTTTGCAT (G->A polymorphism at pos. 8 +
insertion of A at pos. 13)
                                            (SEQ ID NO: 4)
4. ATCGACGACGTTTAGCAT
```

To perform a local alignment of the sequence read GTTTAG against this subsection of the reference DAG, these four sequences could be provided as individual reference sequences to a linear alignment or pattern matching algorithm. The linear alignment or pattern matching algorithm would subsequently identify a best-fit alignment for the sequence read with respect to the four sequences. In this way, systems and methods according to the disclosure may enumerate the possible paths for a reference DAG or subsection of a reference DAG, identify a sequence associated with each possible path, and provide each sequence to an alignment tool (such as those disclosed herein) for alignment with a sequence read.

In another embodiment, the subsection of the reference DAG could be linearized by walking the graph using a sliding window of n bases (wherein n is the length of the sequence read) and performing a comparison of the sequence read to the reference sequence in the window. (Of course, in certain embodiments, the size of the window can be increased to accommodate the possibility of small insertions and deletions in the sequence read.) The walk can similarly be performed using a depth-first search. For example, for the sequence read GTTTAG and subsection of the reference DAG 601 in the embodiment of FIG. 6, a local alignment could proceed as shown in Table 1.

TABLE 1

Depth-First Search Results using a sliding window of n bases and performing a comparison of the sequence read to the reference sequence in the Window.

| #  | Path   | Sequence Read | Comparison | Note |
|----|--------|---------------|------------|------|
| 1  | ATCGAC | GTTTAG | No Match | Start of Graph |
| 2  | TCGACG | GTTTAG | No Match | Includes "G" Polymorphism |
| 3  | CGACGG | GTTTAG | No Match | Includes "G" Polymorphism |
| 4  | GACGGC | GTTTAG | No Match | Includes "G" Polymorphism |
| 5  | ACGGCG | GTTTAG | No Match | Includes "G" Polymorphism |
| 6  | CGGCGT | GTTTAG | No Match | Includes "G" Polymorphism |
| 7  | GGCGTT | GTTTAG | No Match | Includes "G" Polymorphism |
| 8  | GCGTTT | GTTTAG | No Match | Includes "G" Polymorphism |
| 9  | CGTTTG | GTTTAG | No Match | |
| 10 | GTTTGC | GTTTAG | No Match | |
| 11 | TTTGCA | GTTTAG | No Match | |
| 12 | TTGCAT | GTTTAG | No Match | End of Graph |
| 13 | CGTTTA | GTTTAG | No Match | Previous Unfollowed Path Includes "A" Insertion |
| 14 | GTTTAG | GTTTAG | Match    | Includes "A" Insertion |
| 15 | TTTAGC | GTTTAG | No Match | Includes "A" Insertion |
| 16 | TTAGCA | GTTTAG | No Match | Includes "A" Insertion |
| 17 | TAGCAT | GTTTAG | No Match | Includes "A" Insertion End of Graph |
| 18 | CGACGA | GTTTAG | No Match | Previous Unfollowed Path Includes "A" Polymorphism |
| 19 | GACGAC | GTTTAG | No Match | Includes "A" Polymorphism |
| 20 | ACGACG | GTTTAG | No Match | Includes "A" Polymorphism |
| 21 | CGACGT | GTTTAG | No Match | Includes "A" Polymorphism |

TABLE 1-continued

Depth-First Search Results using a sliding window of n bases
and performing a comparison of the sequence read to the
reference sequence in the Window.

| # | Path | Sequence Read Comparison | Note |
|---|---|---|---|
| 22 | GACGTT GTTTAG | No Match | Includes "A" Polymorphism |
| 23 | ACGTTT GTTTAG | No Match | Includes "A" Polymorphism No remaining paths to follow |

Once the walk has completed, the highest scoring matches can be identified to obtain the locally aligned position for the sequence read. As shown in Table 1, a match occurs at the 14$^{th}$ comparison. While a depth-first search is described for traversing the graph, various other searching algorithms or techniques may be used. For example, a breadth-first search could be substituted. Similarly, one could also employ an algorithm following the right-most path, or any previously unfollowed path. Various embodiments are considered to be within the scope of the disclosure.

As previously noted, pattern matching algorithms are particularly well suited for aligning sequence reads to DAGs. As known variations are already present in the graph, the pattern matching algorithm does not need to consider the presence of indels or other variations within a sequence read. Instead, the pattern matching algorithm simply considers each path available through the graph, such as in the manner described above. However, as noted above, while pattern matching algorithms are fast, the performance of such an algorithm (and other local alignment algorithms) can be affected based on the complexity of the DAG surrounding the local alignment position.

Considering DAG Complexity to Select a Local Alignment Tool

The complexity of a DAG at a given region indicates the amount of variation in the reference genome at that position. The complexity of a DAG can be determined in a variety of ways. For example, the complexity of a DAG can be the number of nodes, number of vertices, number of branches, number of possible paths, and the like. Complexity may be determined for a subsection or region of the DAG, or for the entire DAG.

Figure 7:
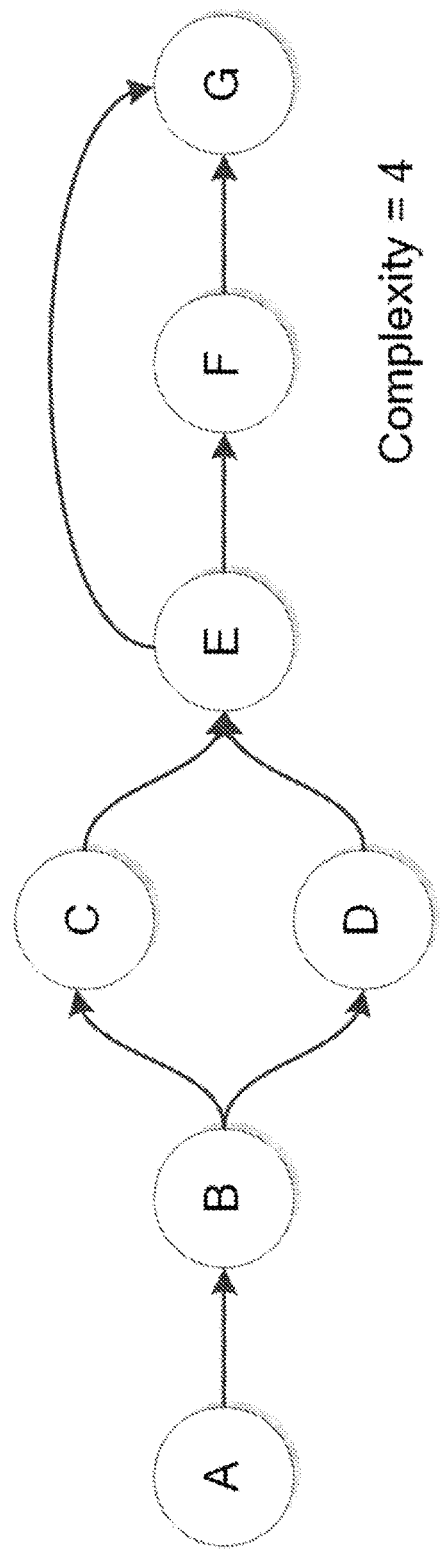
FIG. 7 shows an exemplary DAG representing a single nucleotide polymorphism (C or D) and an insertion (EG or EFG).
Figure 8:
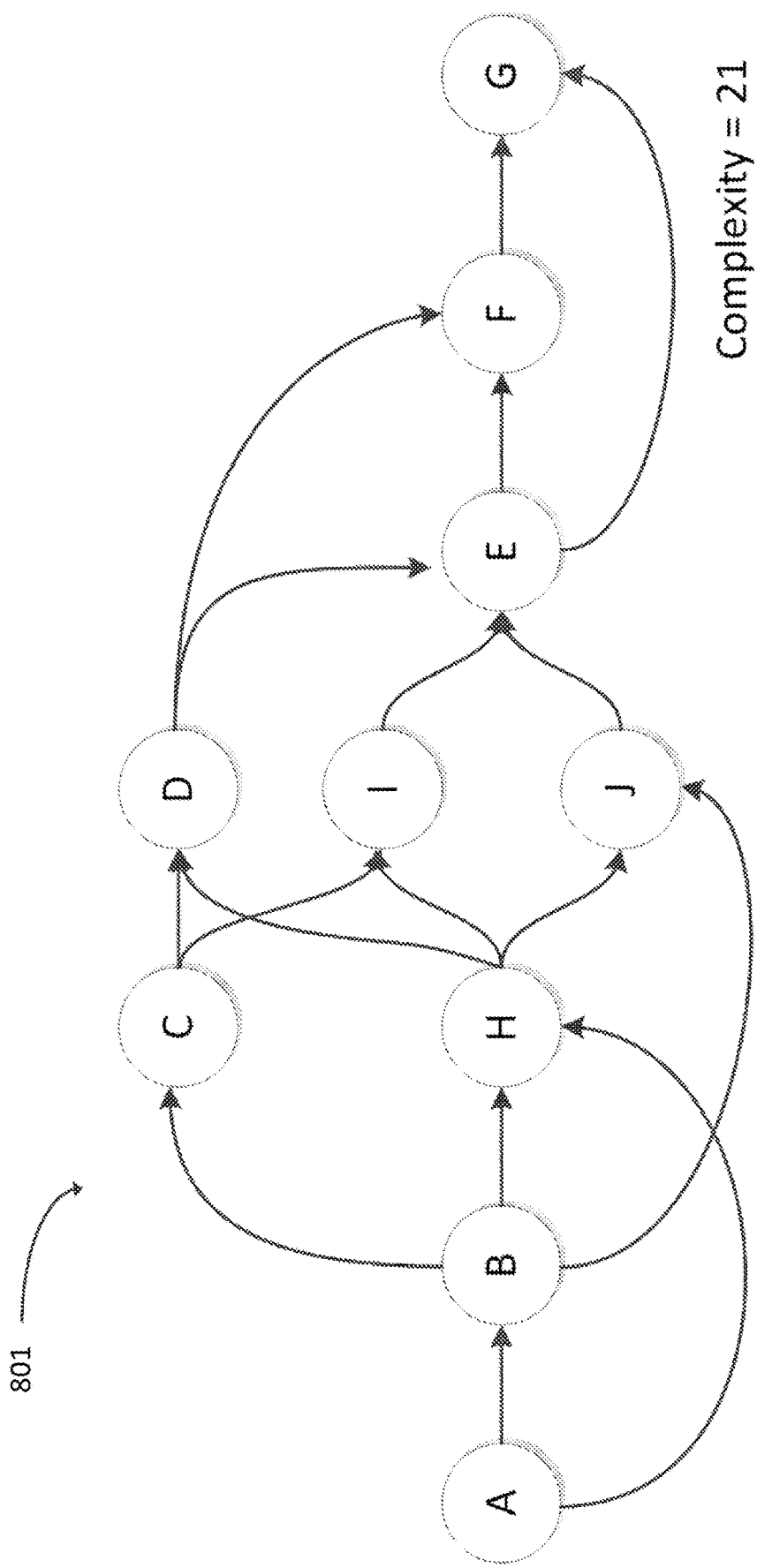
FIG. 8 shows an exemplary DAG representing a highly variable region of the genome that includes information regarding various structural variations, SNPs, and small insertions and deletions.

For example, a DAG 701 shown in FIG. 7 includes information for a single nucleotide polymorphism (C or D) and an insertion (EG or EFG). There are a total of seven nodes and four paths through the DAG. In another example, a DAG 801 shown in FIG. 8 indicates a highly variable region of the genome that includes information regarding various structural variations, SNPs, and small insertions and deletions. In this DAG 801, there are 10 nodes and 21 possible paths.

If there are few paths (e.g., 10 or less, 9 or less, 8 or less, 7 or less, 6 or less, 5 or less, 4 or less, 3 or less 2 or less) through the DAG, then the DAG complexity is low. In these cases, a local linear sequence alignment or pattern matching algorithm may be faster and more efficient than a graph aware algorithm. In these cases, the additional number of paths that can be tested by the algorithm does not significantly impact the advantages in speed gained by using a pattern matching algorithm (e.g., by using a shift table to avoid unnecessary computations). Further, the required number of comparisons can be performed in less processing time than by generating a plurality of matrices for each node, as required by Graph Smith-Waterman. However, if the complexity is high (e.g., 10 or more paths, 10-15 paths, 15 or more paths, 15-20 paths, or 20 or more paths) then the number of paths that must be tested quickly increases. In these cases, Graph Smith-Waterman may be more efficient than a linear sequence alignment or pattern matching algorithm because it does not suffer from the combinatorial explosion problem associated with linearizing complex DAGs.

Figure 9:
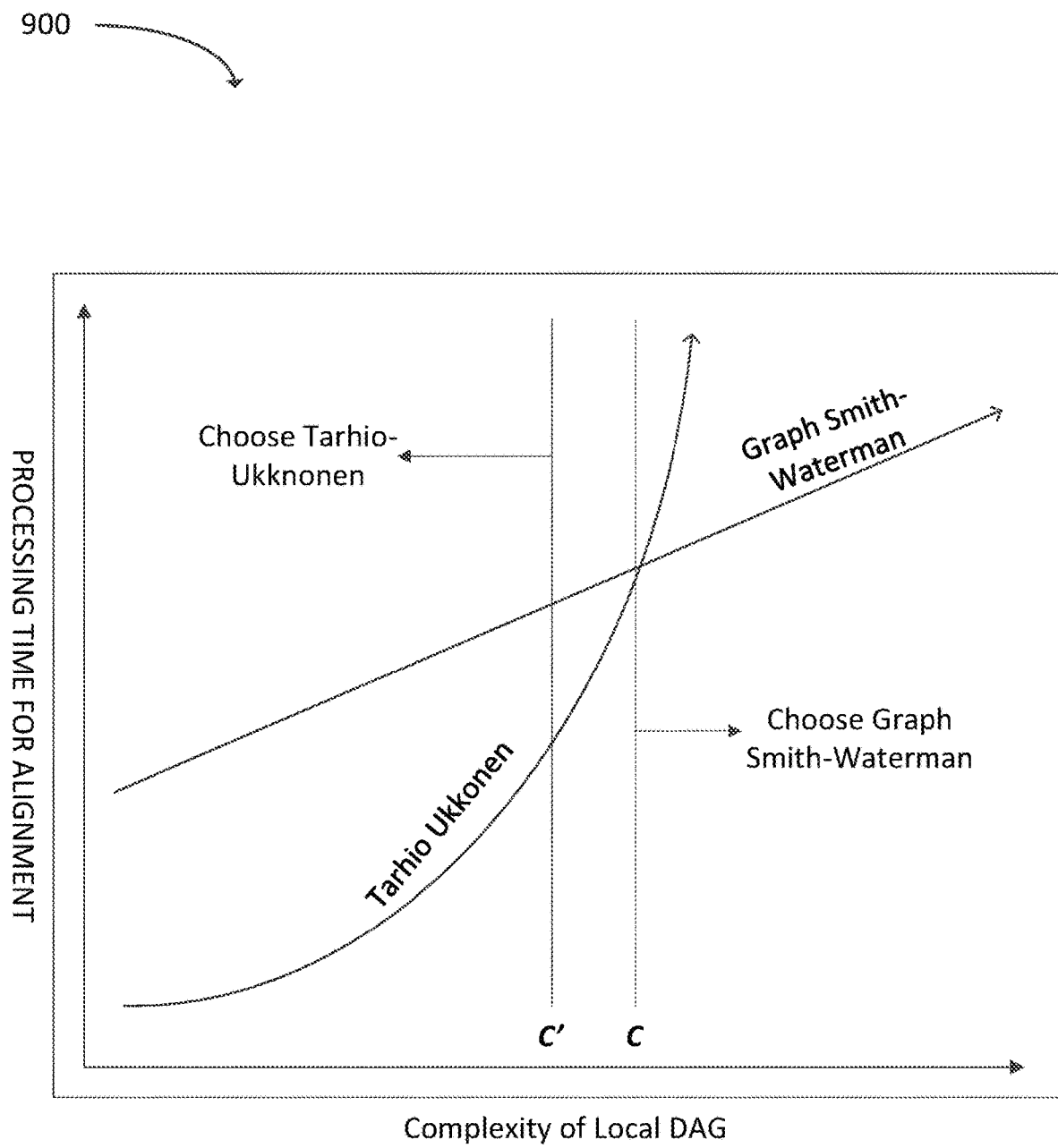
FIG. 9 illustrates the relationship between processing time and DAG complexity for a pattern matching algorithm (such as Tarhio-Ukkonen) and a graph aware alignment algorithm (such as a Graph Smith-Waterman alignment method).

The relationship between the alignment processing time and local DAG complexity is shown in FIG. 9 as a graph 900. Graph 900 illustrates the relationship between processing time and DAG complexity for a pattern matching algorithm (such as Tarhio-Ukkonen) and a graph aware algorithm (such as Graph Smith-Waterman). As shown, at a level of complexity C, performance of Tarhio-Ukkonen and Graph Smith-Waterman is equal and either algorithm may be used without a deviation in performance. Above C, Tarhio-Ukkonen becomes more inefficient due to the large number of paths that must be individually tested, and Graph Smith-Waterman may be preferred. In contrast, below C, Tarhio-Ukkonen is more efficient and requires less processing time.

Even though performance of either algorithm may be comparable at a level of complexity C, other considerations may dictate usage of either algorithm depending on the circumstances. For example, in certain instances, switching local alignment algorithms at a level of complexity C' may be preferable instead of C. As discussed elsewhere, Graph Smith-Waterman is an exact alignment algorithm and thus able to identify gapped alignments between a sequence read and a reference. Thus, even if an approximate pattern-matching algorithm would execute in less time, it may still be preferable to choose Graph Smith-Waterman because the resulting alignment can be superior. In these cases, the ideal level of complexity at which the method chooses either algorithm is based on the acceptable timeliness of performance. As shown in FIG. 9, above C, Graph Smith-Waterman is may be preferable. However, below C, one may also decide to use Graph Smith-Waterman. The consideration is the tradeoff between processing time and improved alignments. Given the scales typically associated with next generation sequencing (e.g., to cover the human genome at 30× coverage, approximately 600 million paired-end 100 bp sequence reads are required), a processing method may account for a level of complexity in which the processing time is reasonable, yet the alignments are able to yield useful information regarding unknown variants.

Price may also be a consideration. For example, cloud computing services such as Amazon AWS and Microsoft Azure offer cloud-based computational resources at a cost. When using these services to align next generation sequence reads against DAGs, one may decide to switch to Tarhio- Ukkonen only when its performance is less than Graph Smith-Waterman in order to reduce processing time and increase cost efficiency.

In certain embodiments, a sequence read could be realigned depending on the resulting quality of the local alignment. For example, if a sequence read has an unknown variation (such as an insertion or deletion), and the complexity of a DAG at a candidate mapping positon is low and a pattern matching algorithm is used, the resulting alignment may have low quality. This is because pattern matching algorithms, while fast, may not gracefully handle unknown variations. In these cases, an optimal alignment algorithm (such as Smith Waterman) could be subsequently performed to accurately identify the variation and improve the local alignment. Similarly, in high entropy or high variability areas of the genome, an optimal alignment algorithm could be substituted for a pattern matching algorithm to improve the quality of the alignment. The quality of an alignment may be expressed according to the Phred scale, for example.

Additionally, in certain embodiments, more than two alignment algorithms may be selected based on the complexity. For example, one may consider using a pattern matching algorithm, an optimal alignment algorithm, and a graph-aware algorithm as complexity increases. In this way, systems and methods according to the invention may select from two, three, or more local alignment algorithms to significantly improve the performance of next-generation sequencing alignment using graph data structures.

Exemplary System

Figure 10:
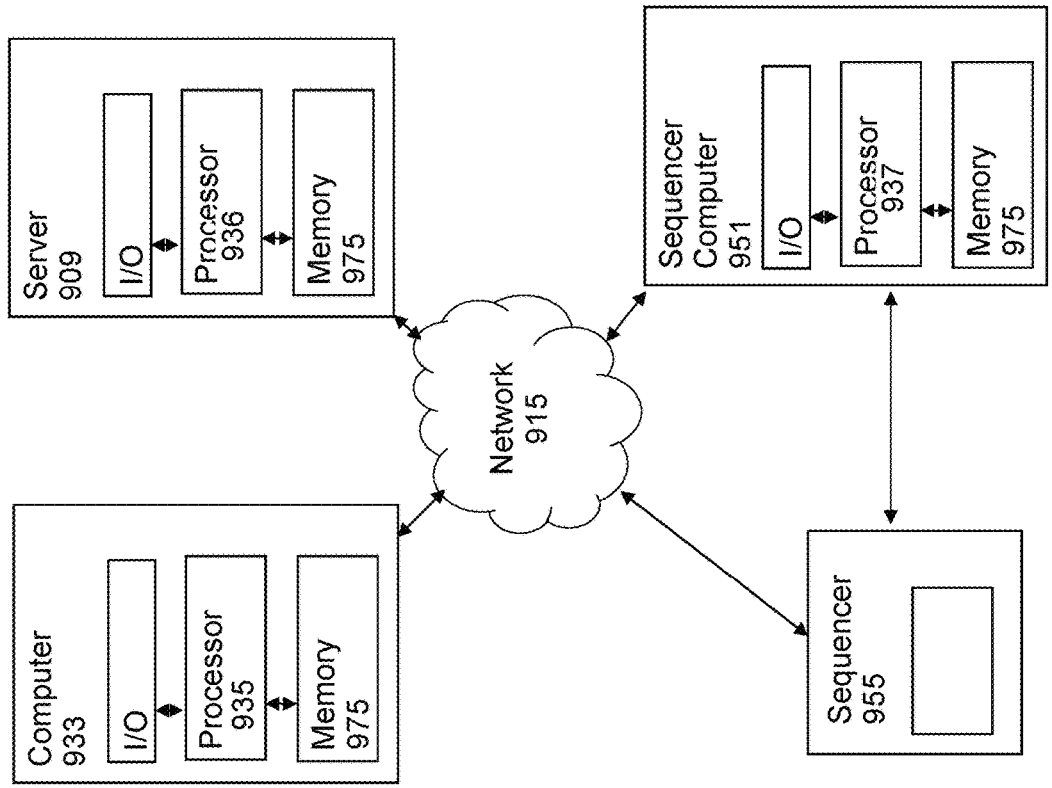
FIG. 10 illustrates a system for implementing the methods diagramed in FIGS. 1 and 2.

FIG. 10 illustrates a computer system 901 suitable for performing methods of the invention. The computer system 901 includes at least one computer 633. Optionally, the computer system 901 may further include one or more of a server computer 909 and a sequencer 955, which may be coupled to a sequencer computer 951. Each computer in the computer system 901 includes a processor 935, 936, or 937 coupled to a memory device and at least one input/output device. Thus the computer system 901 includes at least one processor 935 coupled to a memory subsystem 975 (e.g., a memory device or collection of memory devices). Using those mechanical components, the computer system 901 is operable to obtain a sequence generated by sequencing nucleic acid from a genome of a patient. The system uses the processor to transform the sequence read 103 information into the reference DAG 331.

Processor refers to any device or system of devices that performs processing operations. A processor will generally include a chip, such as a single core or multi-core chip, to provide a central processing unit (CPU). A processor may be provided by a chip from Intel or AMD. A processor may be any suitable processor such as the microprocessor sold under the trademark XEON E7 by Intel (Santa Clara, Calif.) or the microprocessor sold under the trademark OPTERON 6200 by AMD (Sunnyvale, Calif.).

The memory subsystem 975 contains one or any combination of memory devices. A memory device is a mechanical device that stores data or instructions in a machine-readable format. Memory may include one or more sets of instructions (e.g., software) which, when executed by one or more of the processors of the disclosed computers can accomplish some or all of the methods or functions described herein. Preferably, each computer includes a non-transitory memory device such as a solid state drive, flash drive, disk drive, hard drive, subscriber identity module (SIM) card, secure digital card (SD card), micro SD card, or solid-state drive (SSD), optical and magnetic media, others, or a combination thereof.

Using the described components, the computer system 901 is operable to produce a report and provide the report to a user via an input/output device. An input/output device is a mechanism or system for transferring data into or out of a computer. Exemplary input/output devices include a video display unit (e.g., a liquid crystal display (LCD) or a cathode ray tube (CRT)), a printer, an alphanumeric input device (e.g., a keyboard), a cursor control device (e.g., a mouse), a disk drive unit, a speaker, a touchscreen, an accelerometer, a microphone, a cellular radio frequency antenna, and a network interface device, which can be, for example, a network interface card (NIC), Wi-Fi card, or cellular modem.

Preferably the reference DAG is stored in the memory subsystem using adjacency techniques, which may include pointers to identify a physical location in the memory subsystem 675 where each vertex is stored. In a preferred embodiment, the graph is stored in the memory subsystem 675 using adjacency lists. In some embodiments, there is an adjacency list for each vertex. For discussion of implementations see 'Chapter 4, Graphs' at pages 515-693 of Sedgewick and Wayne, 2011, Algorithms, 4th Ed., Pearson Education, Inc., Upper Saddle River N.J., 955 pages, the contents of which are incorporated by reference and within which pages 524-527 illustrate adjacency lists.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

Other implementations are within the scope of the following claims.

What is claimed is:

1. A method, comprising:
using at least one hardware processor to perform:
  accessing data indicative of:
    a sequence read including genetic information; and
    a graph representing a reference genome and variation in the reference genome,
  the graph comprising nodes representing genetic sequences and edges connecting at least some of the nodes;
  identifying a first portion of the graph including a first candidate mapping position;
  selecting, from among multiple alignment algorithms and based on a measure of complexity of the first portion of the graph, an alignment algorithm to use for aligning the sequence read to the first portion of the graph, the multiple alignment algorithms including a first alignment algorithm and a second alignment algorithm different from the first alignment algorithm, the selecting comprising:

determining a number of paths through the first portion of the graph or a number of nodes in the first portion of the graph, selecting the first alignment algorithm as the alignment algorithm to use for aligning the sequence read to the first portion of the graph, when either the number of paths through the first portion of the graph is greater than a threshold number of paths or when the number of nodes is greater than a threshold number of nodes, and selecting the second alignment algorithm as the alignment algorithm to use for aligning the sequence read to the first portion of the graph, when either the number of paths through the first portion of the graph is less than or equal to the threshold number of paths or when the number of nodes is less than or equal to the threshold number of nodes; and aligning the sequence read to the first portion of the graph using the selected alignment algorithm.

2. The method of claim 1, further comprising using the at least one hardware processor to perform:

identifying a second portion of the graph including a second candidate mapping position;

selecting, from among the multiple alignment algorithms and based on a measure of complexity of the second portion of the graph, a second alignment algorithm to use for aligning the sequence read to the second portion of the graph; and aligning the sequence read to the second portion of the graph using the selected second alignment algorithm for aligning the sequence read to the second portion of the graph.

3. The method of claim 2, further comprising using the at least one hardware processor to perform:

determining, based on the alignment of the sequence read to the first portion of the graph and the alignment of the sequence read to the second portion of the graph, whether to align the sequence read to the graph using the first portion of the graph or the second portion of the graph.

4. The method of claim 3, further comprising using the at least one hardware processor to perform:

determining a first measure of quality for the alignment of the sequence read to the first portion of the graph;

determining a second measure of quality for the alignment of the sequence read to the second portion of the graph; and ranking the alignment of the sequence read to the first portion of the graph and the alignment of the sequence read to the second portion of the graph based on the first measure of quality and the second measure of quality.

5. The method of claim 1, further comprising using the at least one hardware processor to perform:

determining the number of paths through the first portion of the graph.

6. The method of claim 5, wherein selecting the alignment algorithm from among the multiple alignment algorithms based on the measure of complexity comprises:

determining whether the number of paths through the first portion of the graph is less than or equal to the threshold number of paths;

when it is determined that the number of paths is greater than the threshold number of paths, selecting the first alignment algorithm of the multiple alignment algorithms; and when it is determined that the number of paths is less than or equal to the threshold number of paths, selecting the second alignment algorithm of the multiple alignment algorithms.

7. The method of claim 6, wherein the threshold number of paths is selected from the group consisting of two paths to twenty paths.

8. The method of claim 6, wherein the first alignment algorithm is a graph-based alignment algorithm.

9. The method of claim 6, wherein the second alignment algorithm is a linear alignment algorithm or a pattern matching algorithm.

10. The method of claim 1, further comprising: determining the number of nodes in the first portion of the graph.

11. The method of claim 10, wherein selecting the alignment algorithm from among the multiple alignment algorithms based on the measure of complexity comprises:

determining whether the number of nodes is less than the threshold number of nodes;

when it is determined that the number of nodes is greater than the threshold number of nodes, selecting the first alignment algorithm of the multiple alignment algorithms; and when it is determined that the number of nodes is less than or equal to the threshold number of nodes, selecting the second alignment algorithm of the multiple alignment algorithms.

12. The method of claim 11, wherein the first alignment algorithm is a graph-based alignment algorithm.

13. The method of claim 11, wherein the second alignment algorithm is a linear alignment algorithm or a pattern matching algorithm.

14. The method of claim 11, wherein the threshold number of nodes is less than or equal to ten nodes.

15. The method of claim 1, wherein aligning the sequence read to the first portion of the graph using the selected alignment algorithm comprises:

generating a plurality of linear sequences based on the first portion of the graph, wherein each linear sequence of the plurality of linear sequences represents a respective path through the first portion of the graph; and aligning the sequence read against each of the plurality of linear sequences using the selected alignment algorithm.

16. The method of claim 15, further comprising using the at least one hardware processor to perform a depth first search of the first portion of the graph to generate the plurality of the linear sequences.

17. A system comprising:

at least one processor; and at least one non-transitory machine-readable memory device storing processor-executable instructions that, when executed by the at least one processor, cause the at least one processor to perform:

accessing data indicative of:

a sequence read including genetic information; and a graph representing a reference genome and variation in the reference genome, the graph comprising nodes representing genetic sequences and edges connecting at least some of the nodes;

identifying a first portion of the graph including a first candidate mapping position;

selecting, from among multiple alignment algorithms and based on a measure of complexity of the first portion of the graph, an alignment algorithm to use for aligning the sequence read to the first portion of the graph, the multiple alignment algorithms including a first alignment algorithm and a second alignment algorithm different from the first alignment algorithm, the selecting comprising:
  determining a number of paths through the first portion of the graph or a number of nodes in the first portion of the graph,
  selecting the first alignment algorithm as the alignment algorithm to use for aligning the sequence read to the first portion of the graph, when either the number of paths through the first portion of the graph is greater than a threshold number of paths or when the number of nodes is greater than a threshold number of nodes, and
  selecting the second alignment algorithm as the alignment algorithm to use for aligning the sequence read to the first portion of the graph, when either the number of paths through the first portion of the graph is less than or equal to the threshold number of paths or when the number of nodes is less than or equal to the threshold number of nodes; and
aligning the sequence read to the first portion of the graph using the selected alignment algorithm.

18. The system of claim 17, wherein the processor-executable instructions are further configured cause the at least one processor to perform:
  identifying a second portion of the graph including a second candidate mapping position;
  selecting, from among the multiple alignment algorithms and based on a second measure of complexity of the second portion of the graph, a second alignment algorithm to use for aligning the sequence read to the second portion of the graph; and
  aligning the sequence read to the second portion of the graph using the selected second alignment algorithm for aligning the sequence read to the second portion of the graph.

19. At least non-transitory one computer readable storage medium storing processor-executable instructions that, when executed by at least one processor, cause the at least one processor to perform:
  accessing data indicative of:
    a sequence read including genetic information; and
    a graph representing a reference genome and variation in the reference genome, the graph comprising nodes representing genetic sequences and edges connecting at least some of the nodes;
  identifying a first portion of the graph including a first candidate mapping position;
  selecting, from among multiple alignment algorithms and based on a measure of complexity of the first portion of the graph, an alignment algorithm to use for aligning the sequence read to the first portion of the graph, the multiple alignment algorithms including a first alignment algorithm and a second alignment algorithm different from the first alignment algorithm, the selecting comprising:
    determining a number of paths through the first portion of the graph or a number of nodes in the first portion of the graph,
    selecting the first alignment algorithm as the alignment algorithm to use for aligning the sequence read to the first portion of the graph, when either the number of paths through the first portion of the graph is greater than a threshold number of paths or when the number of nodes is greater than a threshold number of nodes, and
    selecting the second alignment algorithm as the alignment algorithm to use for aligning the sequence read to the first portion of the graph, when either the number of paths through the first portion of the graph is less than or equal to the threshold number of paths or when the number of nodes is less than or equal to the threshold number of nodes; and
  aligning the sequence read to the first portion of the graph using the selected alignment algorithm.

* * * * *